(12) United States Patent
Sundaresan

(10) Patent No.: US 9,151,733 B1
(45) Date of Patent: Oct. 6, 2015

(54) ACOUSTIC EMISSION SENSOR ARRAY

(75) Inventor: Mannur J. Sundaresan, Greensboro, NC (US)

(73) Assignee: North Carolina A&T State University, Greensboro, NC (US)

(*) Notice: Subject to any disclaimer, the term of this patent is extended or adjusted under 35 U.S.C. 154(b) by 527 days.

(21) Appl. No.: 13/414,092

(22) Filed: Mar. 7, 2012

Related U.S. Application Data

(60) Provisional application No. 61/449,935, filed on Mar. 7, 2011.

(51) Int. Cl.
    *G01N 29/14* (2006.01)
    *G01N 29/24* (2006.01)

(52) U.S. Cl.
    CPC ............ *G01N 29/14* (2013.01); *G01N 29/2475* (2013.01); *G01N 2291/0231* (2013.01); *G01N 2291/0421* (2013.01); *G01N 2291/0422* (2013.01); *G01N 2291/2694* (2013.01)

(58) Field of Classification Search
    CPC .............. G01N 29/14; G01N 29/2475; G01N 2291/0231; G01N 2291/0421; G01N 2291/0422; G01N 2291/2693; G01N 2291/2694
    USPC .......................................................... 73/587
    See application file for complete search history.

(56) References Cited

U.S. PATENT DOCUMENTS

| | | | |
|---|---|---|---|
| 3,787,700 A | 1/1974 | Chasson | |
| 4,088,907 A * | 5/1978 | Jones et al. | 310/333 |
| 4,480,480 A | 11/1984 | Scott et al. | |
| 4,592,034 A * | 5/1986 | Sachse et al. | 367/127 |
| 4,782,701 A | 11/1988 | Proctor, Jr. | |
| 5,195,046 A | 3/1993 | Gerardi et al. | |
| 5,714,687 A | 2/1998 | Dunegan | |
| 5,824,904 A | 10/1998 | Kouhei et al. | |
| 5,894,651 A | 4/1999 | Dvorsky et al. | |
| 5,929,315 A * | 7/1999 | Dunegan | 73/1.82 |
| 5,932,807 A | 8/1999 | Mallart | |
| 6,006,163 A | 12/1999 | Lichtenwalner et al. | |
| 6,021,671 A | 2/2000 | Kami et al. | |
| 6,062,083 A * | 5/2000 | Dunegan | 73/587 |
| 6,076,405 A | 6/2000 | Schoess | |
| 6,173,613 B1 * | 1/2001 | Dunegan | 73/587 |

(Continued)

OTHER PUBLICATIONS

"Detection of Shear Waves in an Aluminum Panel" by Sundaresan and Williams.*

(Continued)

*Primary Examiner* — Laura Martin
*Assistant Examiner* — Rose M Miller
(74) *Attorney, Agent, or Firm* — MacCord Mason PLLC

(57) ABSTRACT

A sensor array for non-destructively monitoring a structure to detect a critical structural event. The sensor array includes at least one discrete AE sensor node for producing an electrical signal in response to a structural event and at least one shear wave sensor assembly. The shear wave sensor assembly includes at least one shear wave sensor. A gate module is connected to the at least one discrete AE sensor node and to the at least one shear wave sensor assembly, whereby the gate module is adapted to pass through the electrical signal from the at least one discrete AE sensor node in response to a pre-determined signal from the at least one shear wave sensor assembly. The sensor array may further include a signal processing module for receiving and processing the discrete AE sensor output signal. In addition, a data collection system may be located downstream of the signal processing module.

20 Claims, 17 Drawing Sheets

(56) References Cited

U.S. PATENT DOCUMENTS

| | | | |
|---|---|---|---|
| 6,370,964 B1 | 4/2002 | Chang et al. | |
| 6,399,939 B1* | 6/2002 | Sundaresan et al. | 250/231.1 |
| 6,626,029 B2 | 9/2003 | Dunegan | |
| 6,923,062 B2 | 8/2005 | Franz et al. | |
| 7,075,424 B1* | 7/2006 | Sundaresan et al. | 340/500 |
| 7,675,820 B2 | 3/2010 | Griffin et al. | |
| 8,170,836 B1* | 5/2012 | Champaigne et al. | 702/187 |
| 2004/0231423 A1 | 11/2004 | Dittrich et al. | |
| 2004/0232911 A1 | 11/2004 | Schlicker et al. | |
| 2009/0326834 A1* | 12/2009 | Sundaresan et al. | 702/34 |

OTHER PUBLICATIONS

ACX (Active Control eXperts); Information from the Internet; copyright 1996-2000.

Asamene, K., Knighton, T., Rajendra, D., Ali, B., Whitlow, T., and Sundaresan, M., "Monitoring the structural integrity and prognostics of composite aircraft components," Proc. of Intl Conf. on Composites for 21st Century, Bangalore, India, Jan. 2011.

Bent, A. A., & Hagood, N. W. (1997). Piezoelectric fiber composites with interdigitated electrodes. Journal of Intelligent Material Systems and Structures, 8(11), 903-919.

Blanas, P., Wenger, M. P., Shuford, R. J., & Das-Gupta, D. K. (Sep. 1997). Active composite materials and damage monitoring. In Proceedings of the International Workshop on Structural Health Monitoring, Stanford University, CA (pp. 199-207).

CeraNova Corporation; Active Composites for Smart Structures; information from internet; copyright 2000.

Chee, C. Y., Tong, L., & Steven, G. P. (1998). A review on the modelling of piezoelectric sensors and actuators incorporated in intelligent structures. Journal of Intelligent Material Systems and Structures, 9(1), 3-19.

Continuum Control Corp., An innovative provider of piezoelectric components and integrated systems for motion control, and vibration suppression, 1999.

Cordell, T. M. (Jul. 1995). Life Management of aging air force aircraft: NDE perspective. In Nondestructive Evaluation of Aging Infrastructure (pp. 34-44). International Society for Optics and Photonics.

Ghoshal, A., Sundaresan, M. J., Schulz, M. J., & Frank Pai, P. (2000). Structural health monitoring techniques for wind turbine blades. Journal of Wind Engineering and Industrial Aerodynamics, 85(3), 309-324.

Hagood, N. W., & Pizzochero, A. (1997). Residual stiffness and actuation properties of piezoelectric composites: theory and experiment. Journal of intelligent material systems and structures, 8(9), 724-737.

Komsky, I. N., & Achenbach, J. D. (Nov. 1996). Ultrasonic imaging of corrosion and fatigue cracks in multilayered airplane structures. In Nondestructive Evaluation Techniques for Aging Infrastructure and Manufacturing (pp. 380-388). International Society for Optics and Photonics.

Lichtenwalner, P. F., Dunne, J. P., Becker, R. S., & Baumann, E. W. (May 1997). Active damage interrogation system for structural health monitoring. In Smart Structures and Materials' 97 (pp. 186-194). International Society for Optics and Photonics.

NASA, Tech Briefs, vol. 23, No. 10, Oct. 1999.

Prosser, Acoustic Emission Structural Health Monitoring, Aviation Safety NRA Meeting, Dec. 17, 1998.

Prosser, W. H., Jackson, K. E., Kellas, S., Smith, B. T., McKeon, J., & Friedman, A. (1995). Advanced waveform-based acoustic emission detection of matrix cracking in composites. Materials evaluation, 53(9), 1052-1058.

Rajendra, D., Esterline, A., & Sundaresan, M. (2010). "A physically based classification approach for identifying AE source mechanism." In SPIE Smart Structures and Materials+ Nondestructive Evaluation and Health Monitoring (pp. 76480Y-76480Y). International Society for Optics and Photonics.

Rajendra, D., Knighton, T., Esterline, A., Sundaresan, M., (2011) "Physics-based classification of acoustic emission waveforms," Nondestructive Characterization for Composite Materials, Aerospace Engineering, Civil Infrastructure, and Homeland Security 2011. Edited by Wu, H. Felix. Proceedings of the SPIE, vol. 7983, article id. 79833H.

Schoess, J. N. (May 1996). Rotor acoustic monitoring system (RAMS): a fatigue crack detection system. In 1996 Symposium on Smart Structures and Materials (pp. 212-218). International Society for Optics and Photonics.

Schulz, et al., Distributed Sensing for Health Monitoring of Composite Materials, Composites in the Transportation Industry Conference, Feb. 14-18, 2000.

Seydel, R. E., & Chang, F. K. (Sep. 1999). Implementation of a real-time impact identification technique for stiffened composite panels. In Proceedings of the 2nd International Workshop on Structural Health Monitoring Ed., F.K. Chang, CRC Press, (pp. 225-233).

Sun, F., Rogers, C. A., & Liang, C. (Apr. 1995). Structural frequency response function acquisition via electric impedance measurement of surface-bonded piezoelectric sensor/actuator. In Proceedings of 36th AIAA/ASME/ASCE/AHS/ASC Structures, Structural Dynamics, and Materials Conference (pp. 3450-3461).

Sundaresan et al., Damage Detection Using a Layer Vibrometer and Active Fiber Composite Patch, Sixth Annual International Conference on Composites Engineering, Orlando, FL, Jun. 27-Jul. 3, 1999.

Sundaresan, M. J., and Shankar, G. "The Use of AET for Classifying Failure Modes in Composite Materials." ASME Winter Annual Meeting, New Orleans, Louisiana, November. vol. 23. 1993.

Sundaresan, M. J., Ghoshal, A., Schulz, M. J., & Pai, P. F. (Oct. 1999). Acoustic emission sensing using piezoceramic and active fiber composite patches. In ASNT 1999 Fall Conference (pp. 11-15).

Sundaresan, M. J., Schulz, M. J., & Ghoshal, A. (2001). Linear location of acoustic emission sources with a single channel distributed sensor. Journal of intelligent material systems and structures, 12(10), 689-699.

Sundaresan, M.J., Ghoshal, A., Martin, W.N., Schulz, M.J., "A Continuous Sensor to Measure Acoustic Waves in Plates," vol. 11, 2001, Journal of Intelligent Material Systems and Structures, pp. 41-56.

Sundaresan, M.J., Ghoshal, A., Schulz, M.J., "A Continuous Sensor for Damage Detection in Bars," Journal of Smart Materials and Structures, 11 (2002), 475-488.

Sundaresan, M.J., Pai, P.F., Ghoshal, A., Schulz, M.J., Ferguson, F., Chung, J., "Methods of distributed sensing for health monitoring of composite material structures," Composites A Journal, 32, 2001, pp. 1357-1374.

Wang, C. S., & Chang, F. K. (Sep. 1999). "Built-in diagnostics for impact damage identification of composite structures." In Proceedings of the 2nd International Workshop on Structural Health monitoring Ed., F.K. Chang, CRC Press, (pp. 8-10).

Whitlow, T., Duwarahn, R., Alam, T., and Sundaresan, M., "Acoustic Emission Based Structural Health Monitoring of Stiffened Panels," Paper No. AIAA-2010-3382, AIAA Infotech@Aerospace 2010 Conference Proceedings, Apr. 20-22, 2010, Atlanta, GA.

Sundaresan M., and Williams, W.B., "Detection of Shear Waves in an Aluminum Panel," Proceedings of SPIE Smart Structures and NDE Conference, Mar. 7-10, 2011, San Diego, CA.

* cited by examiner

| SENSOR TYPE | SOURCE TYPE | DETERMINE LOCATION | REDUCE FALSE POSITIVES |
|---|---|---|---|
| BONDED WAFER AE(<3) | $S_0$ $A_0$ | N | N |
| BONDED WAFER AE($\geq$3) | $S_0$ $A_0$ | Y | N |
| SHEAR WAVE (SINGLE AXIS) | $S_0$ $SH_0$ $A_0$ | N | ANGLE DEPENDENT |
| SHEAR WAVE ($\perp$ AXIS) | $SH_0$ ($S_0 A_0$ CANCELS) | N | Y |
| BONDED WAFER AE($\geq$3) + SHEAR WAVE ($\perp$ AXIS) | $S_0$ $A_0$ + $SH_0$ | Y | Y |

FIG. 17

ACOUSTIC EMISSION SENSOR ARRAY

CROSS-REFERENCE TO RELATED APPLICATIONS

This application claims priority from U.S. Provisional Application No. 61/449,935, filed Mar. 7, 2011, the contents of which are hereby incorporated by reference in its entirety.

STATEMENT AS TO RIGHTS TO INVENTIONS MADE UNDER FEDERALLY SPONSORED RESEARCH OR DEVELOPMENT

Work described herein may have been supported in part by Army Research Office (ARO) Grant No. 210060. The United States Government may therefore have certain rights in the inventions.

COPYRIGHT NOTICE

Contained herein is material that is subject to copyright protection. The copyright owner has no objection to the facsimile reproduction of the patent disclosure by any person as it appears in the Patent and Trademark Office patent files or records, but otherwise reserves all rights to the copyright whatsoever.

FIELD

The present inventions relate generally to non-destructive testing and, more particularly, to an improved sensor array for non-destructively monitoring a structure to detect a critical structural event.

BACKGROUND

The performance of modern-day military helicopters, missiles, tanks, aircraft and other static or dynamic structures is critically dependent on the reliability of advanced composite materials and heterogeneous armor materials. There has been a reluctance to deploy such high performance materials in critical structural applications because of their susceptibility to in-service damage. The damage occurring in these materials may be difficult to track and can propagate quickly during operation of the vehicle or structure, resulting in the loss of the entire vehicle.

Conventional non-destructive evaluation techniques are labor intensive, expensive, error prone, and unworkable for efficient integration into composite and heterogeneous structures. Autonomous integrated Structural Health Monitoring (SHM) techniques are a revolutionary concept in the maintenance of structures. SHM techniques continuously monitor the condition of a structure. Various approaches for SHM under development use piezoceramic (Lead zirconate titanate (Pb[ZrxTi1-x]O3 $0 \leq x \leq 1$), also called PZT,) sensors and actuators that require separate wiring connections for each sensor and actuator element, storage of pre-damage data for each sensor, and instrumentation for active generation and sensing of diagnostic signals. When the structural geometry is complex—e.g., either the structure has varying thickness, curvature, ribs, joints or heterogeneous materials, or damage is located near boundaries of the structure—it becomes difficult to detect small damage using SHM methods. In addition, the number of sensor circuits and computations required increases the overall complexity and cost of the structure.

One approach to this problem is to integrate many fiber-optic strain gauges directly within the structural material. An optical fiber with twenty or more Bragg gratings can measure static and dynamic strains at discrete locations on the structure. An optical analyzer can multiplex over each fiber and each grating to measure strains at a large number of points on a structure. This approach is being implemented on bridges, pressure tanks and other structures. However, fiber optic sensors have limitations when applied to monitoring complex composite structures where damage can occur anywhere on the structure and in any direction. For example, discrete strain measurements can miss damage because the measurement is very localized at the fiber/grating. In addition, an optical analyzer using multiplexing and multiple connections is expensive; measurements are not simultaneous and the frequency bandwidth may be too low to sense Acoustic Emission (AE) signals.

AE sensors are presently suitable for detection of damage at "hot spots." The use of AE measurements for SHM of large structures may have certain advantages since it is a passive sensing technique. Passive sensing methods are simpler and may be more practical than using active interrogation methods. However, present passive acoustic emission and monitoring techniques require bulky instrumentation with numerous channels, long connections, and centralized data analysis. It may be impractical to embed these systems on the structure to operate in the field. Another limitation is that AE waveforms from such sensors are too complicated for purposes of source characterization.

U.S. Pat. No. 6,399,939 issued Jun. 4, 2002 to Sudaresan et al. discloses a sensor array wherein the number of sensors and instrumentation channels required was reduced, by an order of magnitude, while retaining the sensitivity in the high frequency range to detect incipient damage in the structure. The disclosure of this patent and its cited references is hereby incorporated by reference in its entirety.

U.S. Pat. No. 7,075,424 issued Jul. 11, 2006 to Sudaresan et al. discloses a sensor array wherein only one channel of AE instrumentation is required for locating the AE source within a region since the output on a timed scale is used to calculate the location of the critical structural event. The disclosure of this patent and its cited references is hereby incorporated by reference in its entirety.

U.S. patent application Ser. No. 11/271,156, filed Nov. 10, 2005 to Sudaresan et al. discloses sensor assemblies for non-destructively monitoring a structure to detect a structural event. The disclosure of this patent application and its cited references is hereby incorporated by reference in its entirety.

U.S. Provisional Patent Application Ser. No. 61/449,935 filed Mar. 7, 2011 to Sudaresan discloses techniques for identifying source type and the presence of the shear wave, the contents of which are hereby incorporated herein by reference in its entirety.

Thus, there remains a need for a new and improved system for non-destructively monitoring a structure to detect a critical structural event using a sensor array including acoustic emission sensors while, at the same time, includes shear wave sensors which are adapted to prevent false positives of critical structural events.

SUMMARY

The present inventions are directed to a sensor array for non-destructively monitoring a structure to detect a critical structural event. The sensor array includes at least one discrete AE sensor node for producing an electrical signal in response to a structural event and at least one shear wave sensor assembly. The shear wave sensor assembly includes at least one shear wave sensor. In one embodiment, the shear wave sensor assembly includes a pair of shear wave sensors oriented in a plane and at about a 90 degree angle with respect to one another. A gate module is connected to the at least one discrete AE sensor node and to the at least one shear wave sensor assembly, whereby the gate module is adapted to pass through the electrical signal from the at least one discrete AE sensor node in response to a pre-determined signal from the at least one shear wave sensor assembly. The sensor array may further include a signal processing module for receiving and processing the discrete AE sensor output signal. In addition, a data collection system may be located downstream of the signal processing module.

In one embodiment, the sensor array further includes (a) a plurality of discrete AE sensor nodes, each of the discrete AE sensor nodes producing an electrical signal in response to a structural event and (b) a signal adder electrically connected to the plurality of discrete AE sensor nodes, the signal adder receiving and combining the electrical signal from each of the discrete AE sensor nodes to form a single sensor array output signal. Also, the signal processing module may use the time interval between the electrical signals from each of the discrete AE sensor nodes formed into a single sensor array output signal to calculate the location of the critical structural event.

The signal adder and the signal processing module may be connected in series. Also, the sensor array may further include a signal amplifier connected between the signal adder and the signal processing module. In one embodiment, the signal amplifier is an impedance matched amplifier. The sensor array may further include a plurality of individual node signal amplifiers connected between each of the discrete AE sensor nodes and the signal processing module. Each of the node signal amplifiers may be an impedance matched amplifier.

The plurality of discrete AE sensor nodes may be further divided into discrete subgroups, each of the discrete subgroups located at a different structural location. Also, the plurality of discrete AE sensor nodes may be electrically connected in series thereby forming a continuous series connection between each of the discrete AE sensor nodes.

The sensor array may further include a guard array. The guard array may be a guard ring.

The signal processing module may include an input, a filter and an output on a timed scale to calculate the location of the critical structural event. In one embodiment, the filter is at a predetermined band width. The predetermined band width may be calculated according to the Lamb wave propagation characteristics resulting from the acoustic emission pulse at the source location and by identifying one or more non dispersive modes of this lamb wave to locate this acoustic emission source. In one embodiment, the predetermined bandwidth is calculated using an electronic tag attached to each sensor that provides the ID number of the first hit sensor.

Each of the discrete AE sensor nodes may include a piezoceramic sensor. In addition, each of the discrete AE sensor nodes may include an accelerometer. In one embodiment, the piezoceramic sensor for the AE sensor nodes further comprises a plurality of piezoceramic fibers arranged in a planer array, wherein the piezoceramic fibers are aligned substantially parallel to each other.

Turning to the shear wave sensors, each of the pair of shear wave sensors oriented in a plane and at about a 90 degree angle with respect to one another may include a plurality of discrete shear wave sensor nodes adjacent to one another, each of the discrete shear wave sensor nodes producing an electrical signal in response to a structural event. Also, the plurality of discrete shear wave sensor nodes adjacent to one another may be connected in series.

The plurality of discrete shear wave sensor nodes also may be piezoceramic sensors. In one embodiment, the piezoceramic sensors are formed into a strip having a width of less than about 1 mm. In another embodiment, the piezoceramic sensors may be active fiber composites.

The piezoceramic sensors may include a plurality of substantially parallel sensor strips. In one embodiment, the plurality of substantially parallel sensor strips are substantially equal length. Also, the plurality of substantially parallel sensor strips of substantially equal length may be arranged in a rectangular shape or in another embodiment, arranged in a parallelogram shape.

The sensor array may further include a signal adder electrically connected to the plurality of discrete shear wave sensor nodes, the signal adder receiving and combining the electrical signal from each of the discrete shear wave sensor nodes to form a single shear wave output signal from each pair of shear wave sensors oriented in a plane and at about a 90 degree angle with respect to one another.

The sensor array may further include a plurality of shear wave sensor assemblies, each of the shear wave sensor assemblies including at least one pair of shear wave sensors oriented in a plane and at about a 90 degree angle with respect to one another, wherein the plurality of shear wave sensor assemblies are adapted to form a guard array. The guard array may be a guard ring.

In one embodiment, the gate module is connected to the at least one discrete AE sensor node and to the at least one shear wave sensor assembly, whereby the gate module is adapted to pass through the electrical signal from the at least one discrete AE sensor node to the signal processing module in response to a pre-determined signal from the at least one shear wave sensor assembly. The gate module may further include a sub-module for varying the value of the threshold of the pre-determined signal from the at least one shear wave sensor assembly.

The data collection system for the sensor array may include a database module. It also may further include an exception reporting module. The exception reporting module may include a sub-module for setting a predetermined threshold value and a sub-module for sending an alarm when the predetermined threshold value is met. The data collection system may also further include a sub-module for identifying the location of the alarm.

Accordingly, one aspect of the present inventions is to provide a sensor array for non-destructively monitoring a structure to detect a critical structural event, the sensor array including: at least one discrete AE sensor node for producing an electrical signal in response to a structural event; at least one shear wave sensor assembly, the shear wave sensor assembly including at least one shear wave sensor; a gate module connected to the at least one discrete AE sensor node and to the at least one shear wave sensor assembly, whereby the gate module is adapted to pass through the electrical signal from the at least one discrete AE sensor node in response to a pre-determined signal from the at least one shear wave sensor assembly; and a signal processing module for receiving and processing the discrete AE sensor output signal.

Another aspect of the present inventions is to provide an improvement to a sensor array for non-destructively monitoring a structure to detect a critical structural event, the improvement including: at least one shear wave sensor assembly, the shear wave sensor assembly including at least one pair of shear wave sensors oriented in a plane and at about a 90 degree angle with respect to one another; and a gate module connected to the at least one discrete AE sensor node and to the at least one shear wave sensor assembly, whereby the gate module is adapted to pass through the electrical signal from the at least one discrete AE sensor node in response to a pre-determined signal from the at least one shear wave sensor assembly.

Still another aspect of the present inventions is to provide a sensor array for non-destructively monitoring a structure to detect a critical structural event, the sensor array including: at least one discrete AE sensor node for producing an electrical signal in response to a structural event; at least one shear wave sensor assembly, the shear wave sensor assembly including a pair of shear wave sensors oriented in a plane and at about a 90 degree angle with respect to one another; a gate module connected to the at least one discrete AE sensor node and to the at least one shear wave sensor assembly, whereby the gate module is adapted to pass through the electrical signal from the at least one discrete AE sensor node in response to a pre-determined signal from the at least one shear wave sensor assembly; a signal processing module for receiving and processing the discrete AE sensor output signal; and a data collection system located downstream of the signal processing module.

These and other aspects of the present inventions will become apparent to those skilled in the art after a reading of the following description of the disclosure when considered with the drawings.

BRIEF DESCRIPTION OF THE DRAWINGS

FIG. 17 is a comparison of the various combinations of bonded wafer AE sensors and shear wave sensors illustrating combinations which reduce false positives and which also may determine location of a structural event.

DETAILED DESCRIPTION OF EMBODIMENTS

Figure 1:
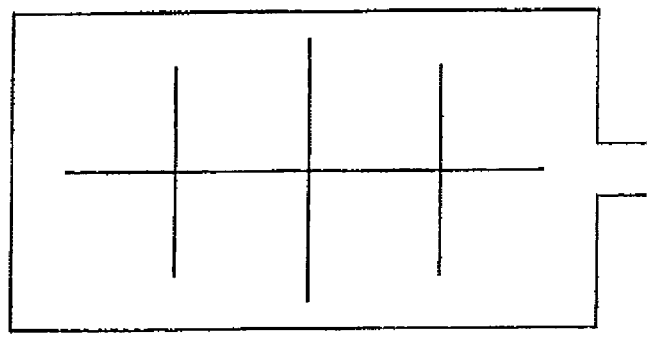
FIG. 1 is a top elevation view of a bi-directional/single node PZT wafer sensor.
Figure 2:
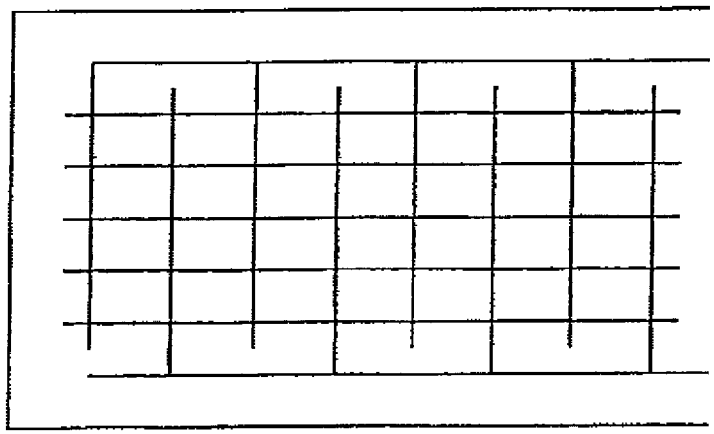
FIG. 2 is a top elevation view of a uni-directional/single node PZT fiber sensor.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Figure 3:
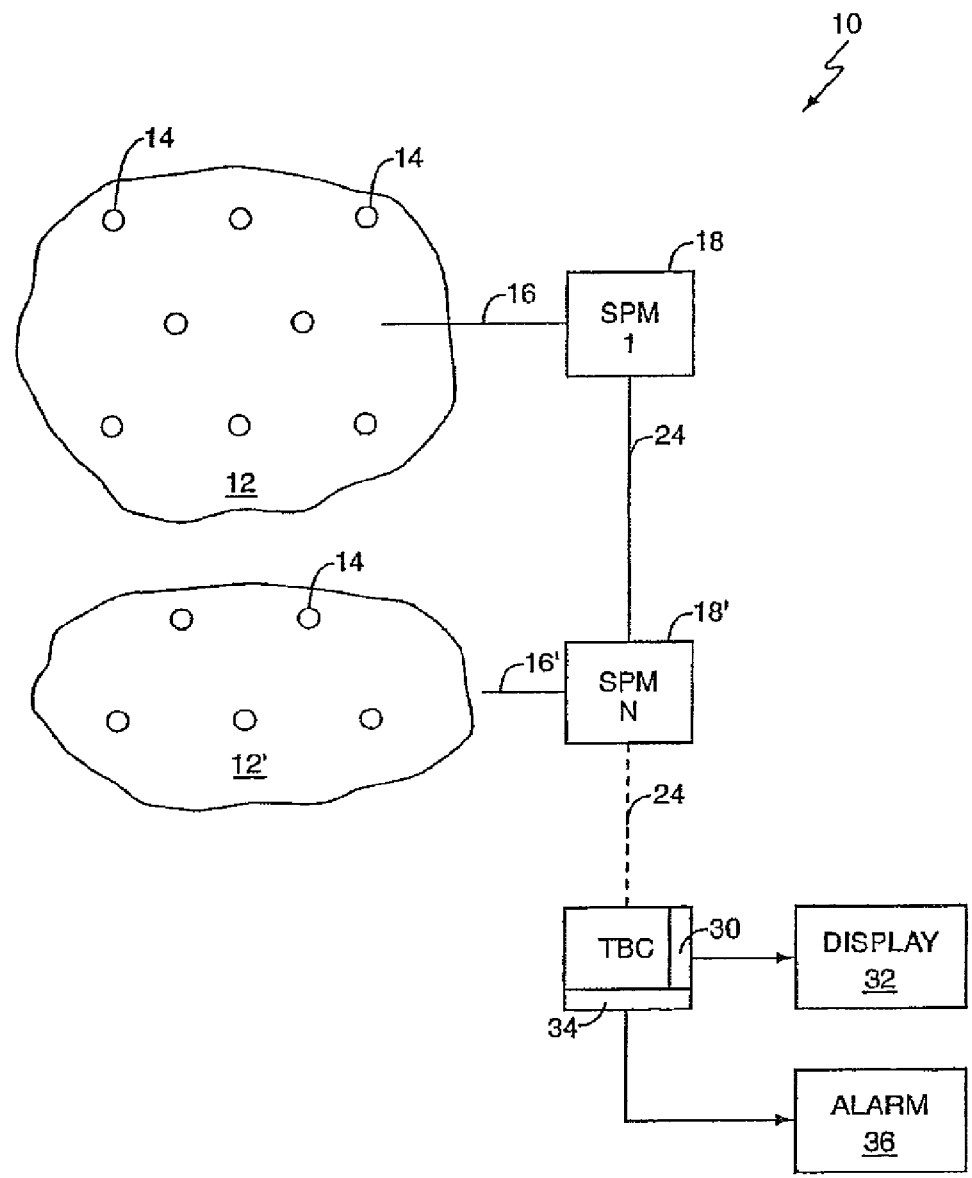
FIG. 3 is a block diagram of a sensor array including a plurality of discrete sensor nodes combined into a single output constructed according to the earlier inventions disclosed in commonly owned U.S. Pat. No. 6,399,939.

Referring now to the drawings in general and FIG. 3 in particular, it will be understood that the illustrations are for the purpose of describing a preferred embodiment of the inventions and are not intended to limit the inventions thereto. As best seen in FIG. 3, a sensor array, generally designated 10, is shown constructed according to the earlier inventions disclosed in commonly owned U.S. Pat. No. 6,399,939. The sensor array 10 includes three major sub-assemblies: a unit cell 12 having a plurality of discrete sensor nodes 14; a signal adder 16 for combining the output of each of the discrete sensor nodes 14 into a single output; and at least one signal processing module 18. Similar signal processing units are commercially available. Among the manufacturers of such units is Endevco Corporation, located in San Juan Capistrano, Calif.

Figure 4:
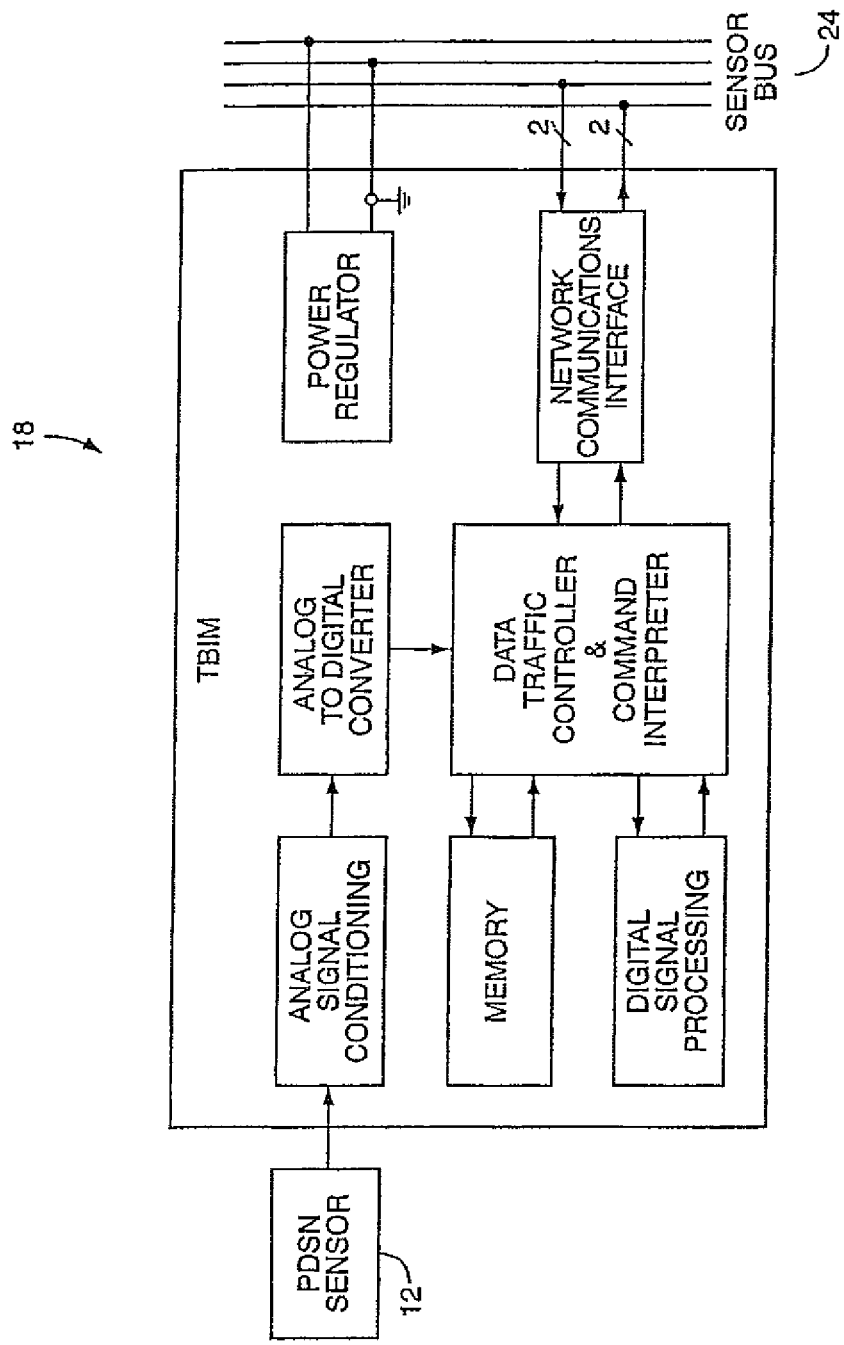
FIG. 4 is an enlarged block diagram of the signal processing module for the sensor array shown in FIG. 3.

As best seen in FIG. 4, an embedded electronic signal processing module 18 conditions the AE signal and performs the data processing. The signal processing module 18 itself is made of an analog ASIC (Application Specific Integrated Circuit), for analog signal conditioning, and a digital ASIC which performs the quantification, pattern recognition, timing, and short time data storage.

As best seen in FIG. 3, a digital data bus 24 provides communication between the signal processing modules 18 and the CPU 30. Further, this bus also powers the signal processing modules 18. The Transducer Bus Controller (TBC) is located in the CPU 30.

The CPU 30 assembles the processed information sent by the sensor nodes 14, and assesses any damage growth that may be occurring in the structure. A special feature of the earlier inventions disclosed in commonly owned U.S. Pat. No. 6,399,939 is that the acoustic emission data processing takes place within the respective signal processing modules 18, and only the processed information is communicated outward through the interface bus 24. Furthermore, the fibers are connected in either series, parallel, or a combined series/parallel configuration to tailor the sensitivity of the sensor nodes 14 and match the environmental conditions under which it is operating. Bi-directional communication between the signal processing modules 18 and the CPU 30 takes place over the single digital data bus 24, thus eliminating cumbersome cables.

In operation, the CPU 30 initializes all sensor nodes 14, including their short-term clocks. The CPU 30 then queries each sensor node at time intervals of the order of a few tens of seconds to download the gathered information. The signal processing modules 18 and the sensor nodes 14 perform the digitization and analysis of the AE signals and store in a tabular form within its memory only those processed data that are recognized as related to damage growth for uploading to the CPU 30.

Among the parameters stored in the signal processing modules 18 are the time of occurrence of the AE event, energy content of the AE event, and the amplitude, duration, pattern, and other relevant parameters of the AE signal envelope. The TBC addresses each signal processing module 18 sequentially to upload the processed information from the signal processing modules 18, 18' permanently stored in CPU 30.

Figure 5:
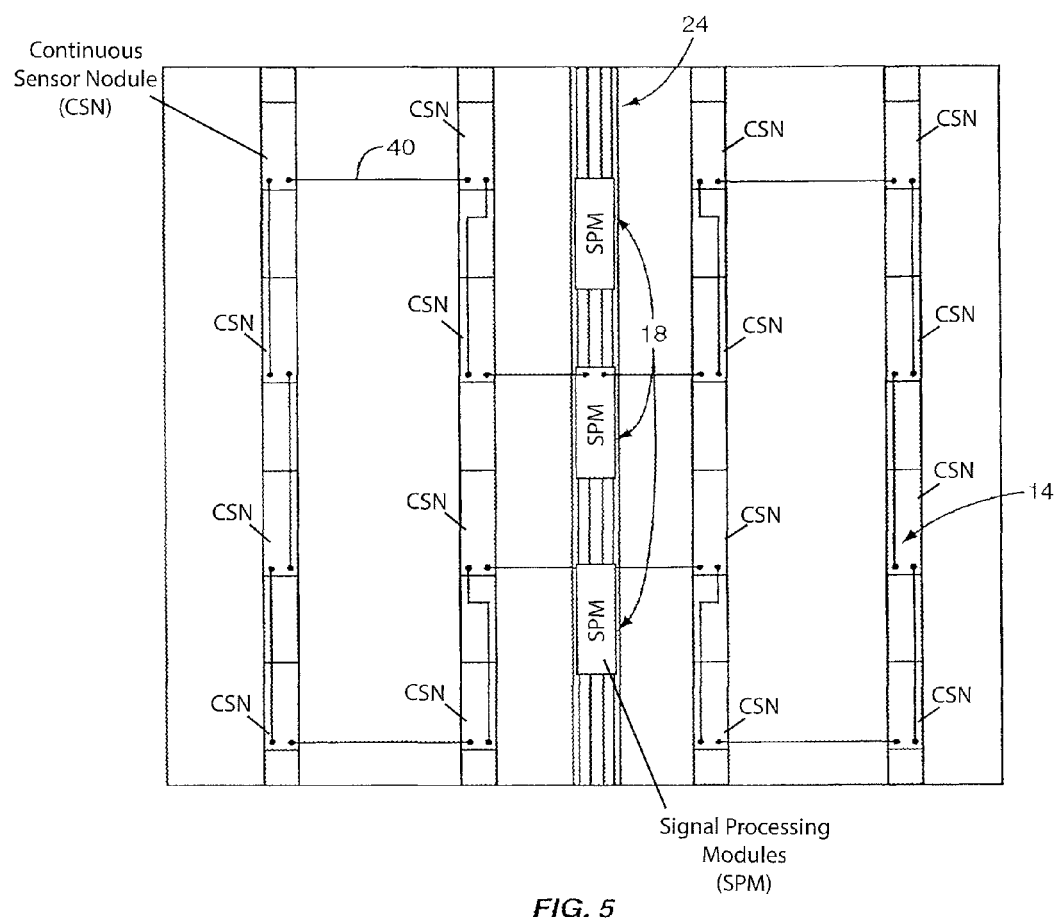
FIG. 5 is a top elevation view of the PZT fiber sensor array having a plurality of discrete sensor nodes connected in series and combined into a single output constructed according to the earlier inventions disclosed in commonly owned U.S. Pat. No. 6,399,939.

As best seen in FIG. 5, the collection of sensor nodes 14 forms a unit cell 12 of a 'smart' composite material. The sensor array 10 can be constructed by embedding tens or hundreds of these sensor nodes 14 in laminated composite or textile composite structures. In one embodiment, each of these sensor nodes 14 is formed from piezoceramic tapes whose segments act as independent sensor nodes 14 that detect damage to the structure by measuring AE waves generated by cracks in the material or breakage of fibers. The piezoceramic fibers can also potentially measure dynamic strains within the structure, which is useful for monitoring and regulating load paths within the structure to extend its safe life.

Active Fiber Composite (AFC) materials using PZT fibers (developed at MIT and commercialized by Continuum Control Corporation, Billerica Mass.) or ribbons (recently developed by Cerallova Corporation, Franklin Mass.) are preferably used to construct long continuous sensors. Interdigitated (IDT) electrodes are used to pole and electrically connect the sensor. The AFC is thermally stable, has a long fatigue life, provides great flexibility in tailoring and designing a sensor material, and is strong and rugged enough to be used on helicopters, in armor, and in layered composites. Because labor comprises most of the cost of producing the sensor tape, the use of a single ribbon effectively replaces six circular fibers, while still retaining the advantages of the fibers, and significantly reduces the cost of the distributed sensors.

Overall, the combination of fine piezoceramic fibers or ribbons with a flexible matrix provides a sensor material that is more robust and has a higher ultimate strain than the monolithic ceramics. The use of fibers or ribbons retains most of the stiffness of monolithic piezoceramic patches, and the unidirectional alignment creates the desired sensing/actuation in a single direction. The active fibers and structural fibers can be mixed within a single ply or can form separate plies in a composite. The overall laminate properties are found by a layer-wise integration of the constitutive equations for the layers. These properties are used in wave propagation simulations to determine the dynamic response of the sensor composite.

The electrode configuration can be designed to pole the fibers axially or through their thickness. Thin foil conductors (IDT electrodes) oriented perpendicular to the fibers are used on the top and bottom of the fibers. The conductors are used for both electroding and poling. The advantages of these designs are: (a) if the sensor is poled through the thickness of the fibers, the electrodes are easy to manufacture; (b) non-conductive structural fibers can be mixed with the sensor fibers, or conductive fibers can be put in adjoining layers; (c) the sensor can measure dynamic strains above 0.5 Hz.; (d) the sensor can be one cell of the system and AEs can be detected from all segments simultaneously; (e) the electrodes are deposited directly on the active fiber for ease of manufacturing and to allow a higher signal output when operating in the low field range; (f) ribbons which are larger than fibers and easier to fabricate can be used instead of fibers, making electroding easier and polarization more uniform; and (g) once encapsulated in a matrix, the ribbon can be woven as a straight fiber into textile composites. Both transverse and axial poling concepts are possible. In conventional AFCs, the electrodes are placed on the matrix above the fibers to prevent concentrations of the electric field in the fiber that can lead to locally high strains and fiber breakage. Because the fibers are used for sensing and not actuation, fatigue due to high electric field concentrations that normally necessitates use of the electroding above the fibers is absent. The electrodes are used for directly poling the sensor material.

Figure 6:
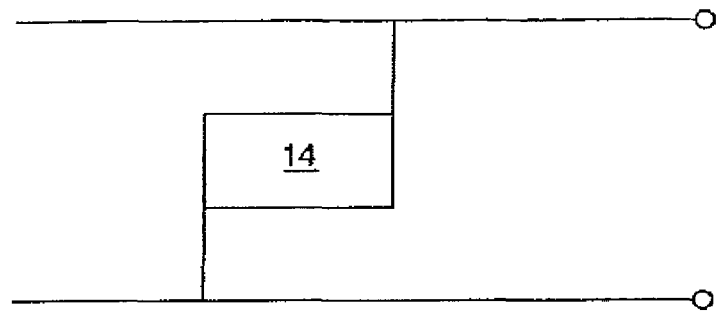
FIG. 6 is a simplified schematic of the bi-directional/single node PZT wafer sensor of the prior art, and the prior-art uni-directional/single node PZT fiber sensor shown in FIGS. 1 and 2.
Figure 7:
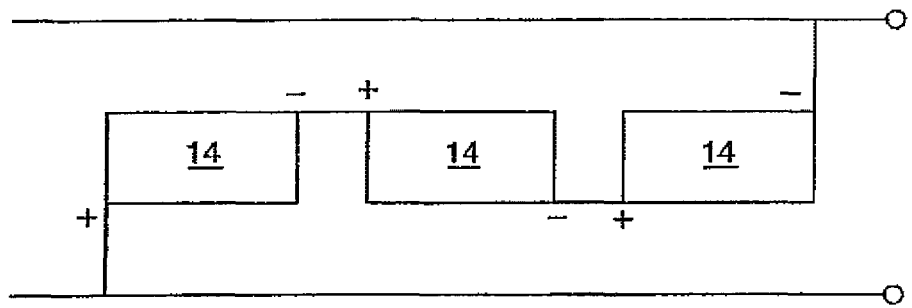
FIG. 7 is a simplified schematic of the sensor array shown in FIG. 5 that includes a plurality of discrete sensor nodes combined into a single output constructed according to the earlier inventions disclosed in commonly owned U.S. Pat. No. 6,399,939.

As best seen in FIG. 6 (the prior art) and FIG. 7 (the earlier inventions disclosed in commonly owned U.S. Pat. No. 6,399,939), the initial modeling that was performed to study the composite couples the elastic equations of a bar or plate structure to the piezoelectric constitutive equations and a parallel tuning electric circuit.

The piezoelectric equations to model a PZT or AFC sensor are:

$$\begin{bmatrix} D \\ T \end{bmatrix} = \begin{bmatrix} \varepsilon^S & e \\ -(e)^t & c^E \end{bmatrix} \begin{bmatrix} E \\ S \end{bmatrix} \quad (1)$$

where D is the electric displacement in coulombs/m$^2$, T is the stress in N/m$^2$, E is the electric field in volts/m, S is the strain, $\in^S$ is the clamped dielectric in Farads/m, e is the induced stress constant in Coluomb/m$^2$ or equivalently N/(m*volt), t is transpose, and c$^E$ is the constant field stiffness in N/m$^2$.

Considering a single axis, the equations in (1) are represented as:

$$D_j = \left( \varepsilon^S E(t) + e \frac{\partial w(x_j, t)}{\partial x} \right) \mathrm{sgn}(j) \quad (2)$$

$$i_{gj} = \left[ C_j \dot{V}_o / K + e \frac{\partial^2 w(x_j, t)}{\partial x \partial t} A_c \mathrm{sgn}(j) \right] \quad (3)$$

where j represents the jth segment of the sensor, w is the longitudinal displacement, V is the voltage, C is the capacitance of the piezoceramic, and the sgn function allows connection of the segments with positive or negative polarities. An electric circuit representing equations (2-3) for series connectivity is shown in FIG. 7.

An electrical parallel tuning circuit is connected to the acoustic emission sensor circuit to filter out the ambient vibration response to more accurately sense the acoustic emissions from cracks.

The combined equations for the electrical model of the AFC sensor and the connected tuning circuit are:

$$\begin{bmatrix} L_s & 0 \\ -L_p & L_p \end{bmatrix} \begin{bmatrix} \dot{i}_l \\ \dot{i}_s \end{bmatrix} + \begin{bmatrix} L_p/(R_p N C_p) & 0 \\ 0 & R_s \end{bmatrix} \begin{bmatrix} \dot{i}_l \\ \dot{i}_s \end{bmatrix} + \begin{bmatrix} 1/(NC_p) & 1/(NC_p) \\ 0 & 1/C_s \end{bmatrix} \begin{bmatrix} i_l \\ i_s \end{bmatrix} = \begin{bmatrix} -\frac{A_e e}{NC_p} \sum_{j=1}^{ns} w_{xt}^j \text{sgn}(j) \\ 0 \end{bmatrix} \quad (4)$$

where is and il are the currents in the tuning circuit, R, L, $C_s$ are the circuit parameters, $C_p$, $A_e$, e are the sensor piezoceramic material parameters, and N, $w_{xt}^j$, sgn(j) are the number of sensor nodes, the strain rate at node j, and sign of the connectivity of node j.

An elastic model of a bar or plate is used to simulate the response of the sensor material subjected to AE or other excitation. The plate with the segments is shown in FIG. 9. The segments S1, S2, S3, S4, ... S16 model the sixteen sensor segments of one fiber tape in the composite shown in FIG. 3. Since the AFC is poled using the electrodes, each segment acts as a uniform sensor. The segments can be spaced and connected in alternating polarity to cancel low frequency (<100 KHz) structural vibrations and the length of the segments can be matched to the half wavelength of the dominant stress waves to be measured.

This approach uses the continuous nature of the sensor as a spatial filter to cut-off the low frequency response that masks the AE response. If small segments are used, the continuous sensor can be designed similar to an acoustic wave filter to measure Lamb waves produced from damage propagation. Organic composites produce extensive AEs in the presence of damage. Thus, monitoring of AE in composites can be used as a passive method for damage detection. AEs in thin composite structures propagate as Lamb or plate waves. The two plate modes of AE waves observed in AE signals are the symmetrical, or extensional, wave and the anti-symmetric, or flexural, mode. Extensional plate waves contain higher frequency components and occur first in the signal, whereas the flexural waves contain lower frequency components, have higher amplitudes, and occur later in the wave. The extensional waves are non-dispersive (i.e., the wave velocity is independent of the wave number) and these plate waves can travel longer distances than dispersive waves. The flexural waves, on the other hand, are dispersive in nature and damage is more difficult to detect using these waves because the phase velocity and amplitudes change with temperature and small variations in boundary conditions.

Figure 8A:
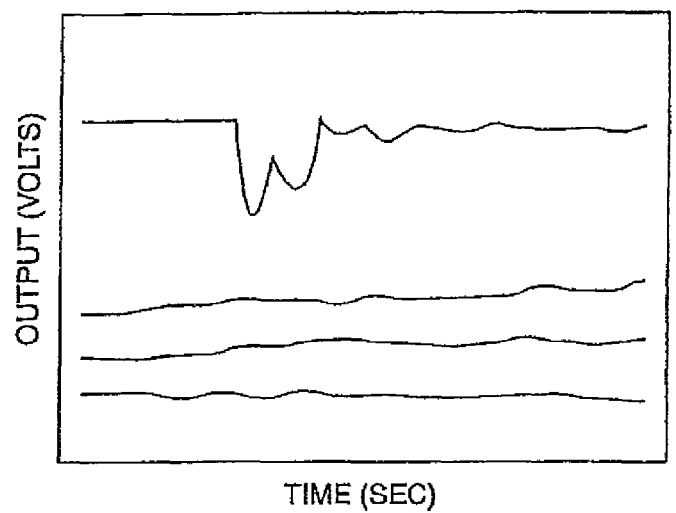
FIGS. 8A and 8B are graphs illustrating the effect of adding a plurality of discrete sensor node outputs into a single output.
Figure 8B:
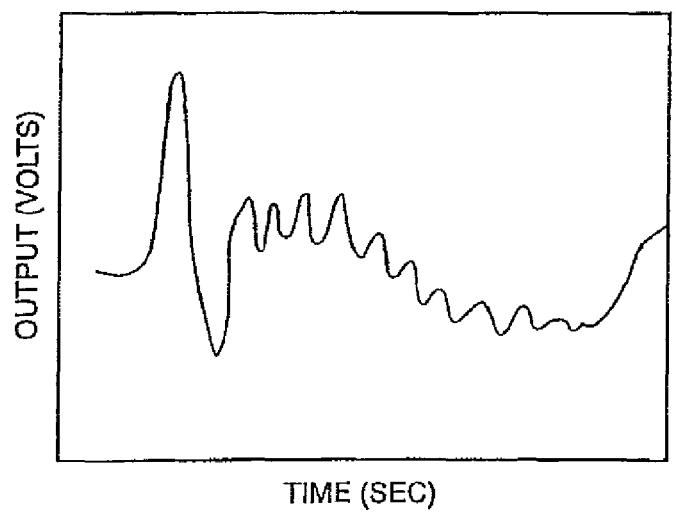

As best seen in FIGS. 8A and 8B, experiments have been performed to verify the characteristics and potential of the continuous sensor material. An AE event was simulated by breaking a pencil lead near sensor 1, and AE waveforms corresponding to four sensors were recorded using a digital oscilloscope, as shown in FIG. 8A. Sensor 1, which was nearest to the simulated AE source, registered the highest signal magnitude, and, more significantly, had higher frequency components present in the signal. Sensors 2, 3 and 4 had progressively fewer high frequency components in the signal, because high frequency components attenuate as a function of distance traveled more rapidly than low frequency components. Frequency components above 100 kHz were almost totally absent in these three sensors.

In practice, frequency components that are higher than 100 kHz can provide valuable information about the AE source. Obtaining those frequency components, however, would require a large number of AE sensors to monitor most structures. The weight, cost, and complexity of such a multichannel instrument may be prohibitive.

Next, a distributed sensor was formed by connecting the four sensors to a single channel of a digital oscilloscope. A signal was generated by breaking a pencil lead near sensor 1. The signal detected from this arrangement is shown in FIG. 8B. The response of the continuous sensor was reduced in amplitude, but the high frequency components were preserved intact and the amplitude levels were still adequate for AE sensing. In this experiment, the optimal circuit design was not used. Had the optimal design been used, it would have increased the voltage output of the continuous sensor to be equal or greater than the output of a single sensor near the pencil lead break. In addition, smaller sensors would be used in practice.

Figure 9A:
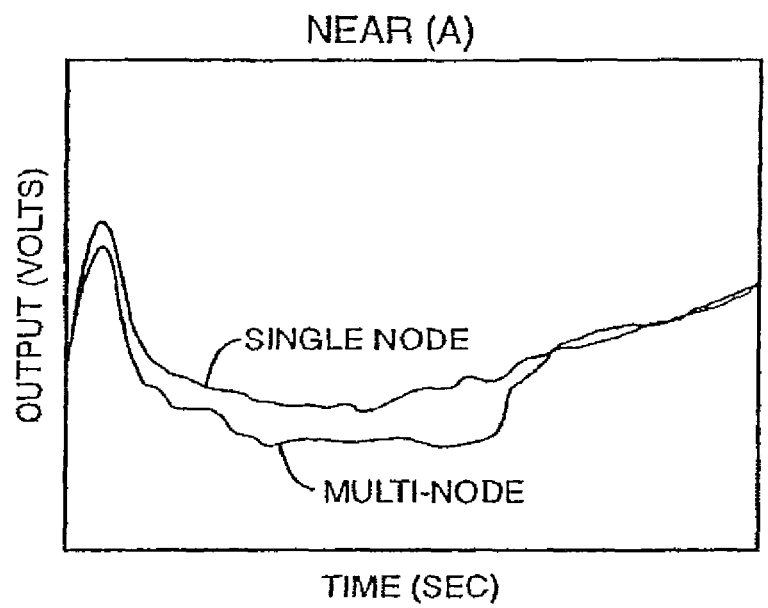
FIGS. 9A and 9B are graphs illustrating the difference between the response of a conventional single node sensor and the response of a multi-node sensor, and their dependence on the location of the structural event.
Figure 9B:
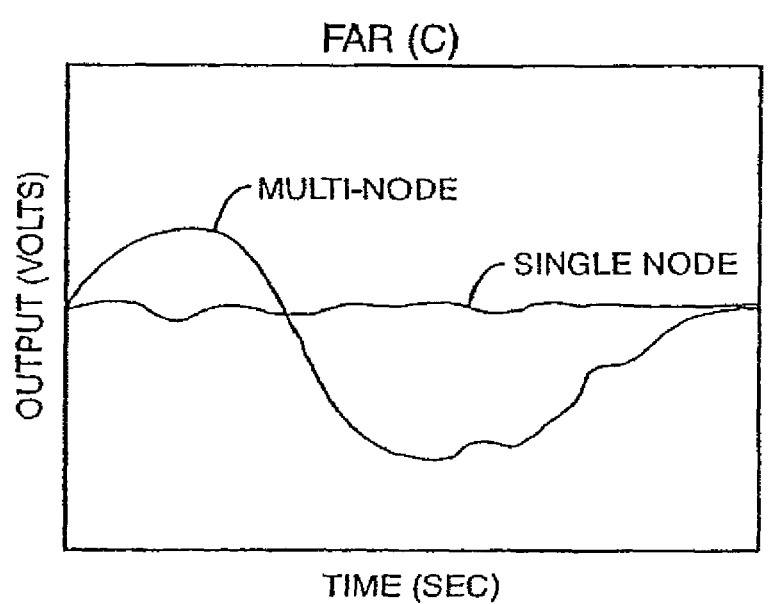
Figure 9C:
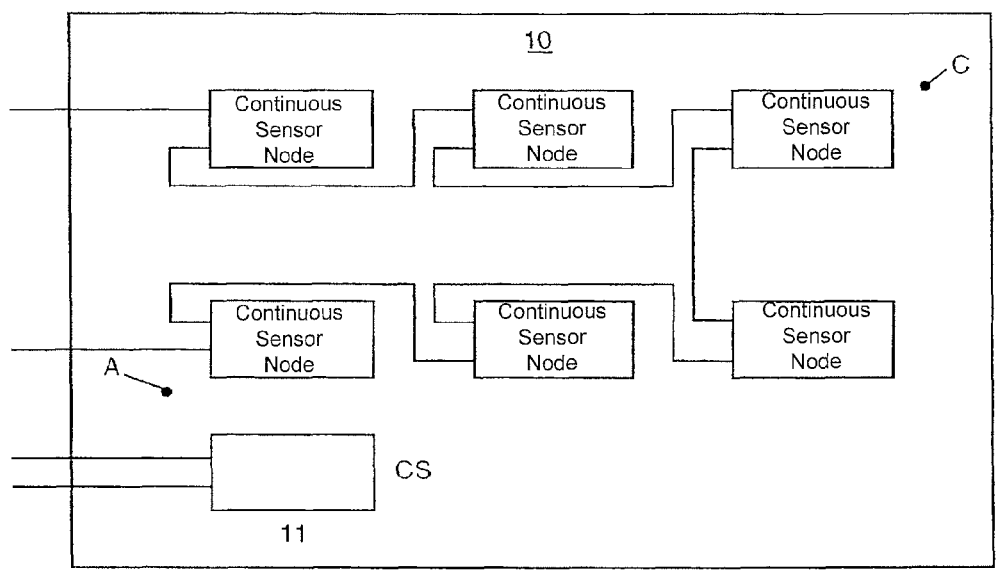
FIG. 9C is a schematic diagram showing the positions of a sensor array of the earlier inventions disclosed in commonly owned U.S. Pat. No. 6,399,939 and a single sensor relative to acoustic emission events.
Figure 10:
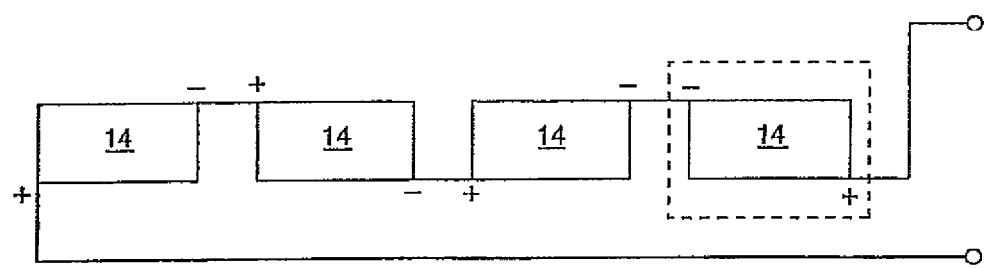
FIG. 10 is a simplified schematic of an alternative embodiment of the sensor array constructed according to the earlier inventions disclosed in commonly owned U.S. Pat. No. 6,399,939 as shown in FIG. 5, including a plurality of discrete sensor nodes combined into a single output.

As best seen in FIGS. 9A and 9B, the output of a continuous sensor array 10 was compared to that of a single PZT sensor 11 for detecting an acoustic emission on a fiberglass panel, shown in FIG. 9C. A pencil lead break at location A in FIG. 9C is detected by both the continuous sensor array 10 and the conventional sensor 11. In contrast, the sensor response due to a pencil lead break at location C in FIG. 9C shows that the continuous sensor array 10 captures the signal while the conventional sensor 11 at CS cannot sense an AE signal that is originating at a point distant from the sensor.

In operation, the continuous highly distributed sensor system can monitor entire structures with a single digital data bus 24 and can thus eliminate the bulky coaxial cables and greatly reduce the hardware and communication needs for a field deployable health monitoring system. To illustrate this, consider an AE event occurring at a random location along a straight-line segment of length L, while this segment is monitored through N equally spaced AE sensors. The maximum distance that the AE signal travels to reach the closest sensor is d=L/(2N). The number of sensors required would be determined by the exponential rate of attenuation of AE voltage signals given by $V = A_o e^{-Kd}/N^a$ where $A_o$ is a signal amplitude coefficient, a is an exponent, and K is a material-dependent decay constant. The sensor array of the earlier inventions disclosed in commonly owned U.S. Pat. No. 6,399,939 is able to minimize the exponents d and a in the above equation, thereby maximizing the possibility of detecting an acoustic event.

In order to train the sensor network, a procedure of calibrating each unit cell can be established. Although the different unit cells attached to a structure may be similar to each other, the dynamics and wave propagation characteristics may vary from point-to-point on the structure. Unless each signal processing module takes these differences into account when reducing the data, errors can be introduced in the quantification of the AE activity. The calibration procedure could establish the threshold levels, data acquisition time window, and other related parameters.

Finally, the software in the CPU 30 will be robust enough to identify the failure of a sensor or signal processing module 18. Redundancy can be built into the sensor network, such that most damages will be detected by more than one unit cell.

Among the advantages provided by the sensor array 10 of the earlier inventions disclosed in commonly owned U.S. Pat. No. 6,399,939 are: (i) a drastic reduction of the weight, cost, and complexity of instrumentation; (ii) increased probability of detection of the acoustical event due to the reduction in the source-to-sensor distance; and (iii) a more faithful retention of the acoustical signature, including the high frequency components, of the source event in the signal transmitted from the distributed sensor, due to minimization of the source-to-sensor distance.

Since the high frequency components of an AE signal attenuate much faster than the low frequency components, the signal from the sensors will have little resemblance to the source event if the travel distance d is long. Conventional AE techniques quickly become impractical for most field-deployable health monitoring applications, as they require as many independent data acquisition channels as the number of sensors.

With the active composite continuous sensor of the earlier inventions disclosed in commonly owned U.S. Pat. No. 6,399,939, an entire structure can be monitored by a group of continuous sensors or unit cells with N sensing elements, all connected to a single digital data acquisition bus. By increasing the number of sensor elements, it is possible to have access to the leading edge of the AE waveform before it is dispersed. Such access is crucial in identifying the source mechanisms and estimating the source magnitude. The AE source can be located within the region of a given distributed sensor and network algorithms will be developed to locate the damage more precisely for subsequent closer inspection and repair.

Certain modifications and improvements will occur to those skilled in the art upon a reading of the foregoing description. By way of example, the electrode pattern—specifically, the width and spacing of the AFC sensor segments—can be designed to optimize the voltage and current output of the sensor for a particular application. Transverse electroding and poling can be used instead of interdigital electrodes and can simplify the design and reduce the cost of the AFC sensor segments.

The continuous sensor segments of the earlier inventions disclosed in commonly owned U.S. Pat. No. 6,399,939 can also be connected in four possible combinations to tailor the sensor characteristics, such as signal level and spatial filtering, for specific applications. The four combinations are: (i) an aligned series connection—i.e., (+−)(+−)(+−)(+−) . . . ; (ii) an alternating series connection—i.e., (+−) (−+) (+−)(−+) . . . ; (iii) an aligned parallel connection in which all positive terminals are connected to a common positive point and all negative terminals to a separate, common negative point; and (iv) an alternating parallel connection in which the parallel connection for the adjacent sensor nodes are reversed.

Besides acoustic emissions, the sensor array of the earlier inventions disclosed in commonly owned U.S. Pat. No. 6,399,939 can measure different events—including peak strains, peak vibration levels, and stress wave propagation from impacts on the structure—that are pertinent to structural health monitoring. The large area coverage and simultaneous sensing can localize the event to a particular unit cell. The sensor array can be configured for integration into composite materials or attachment to the surface of metallic structures such as an aircraft. By having segments of the sensor array connected with different directional sensitivity, the unidirectionality of the active fiber composite sensor material can also be used to determine the location of events.

The individual sensor elements or nodes may also include an addressable switch that can be used to include or exclude that sensor element from the network of the sensor, thus providing a self-configuring sensor continuous sensor that can automatically adapt to operating conditions. The local processor can have the ability to address the switch and to configure the network of sensors to be employed at a given stage to monitor structure health. Communication between the local processor and the individual sensor nodes is established by either a local digital data bus or the signal leads.

Figure 11:
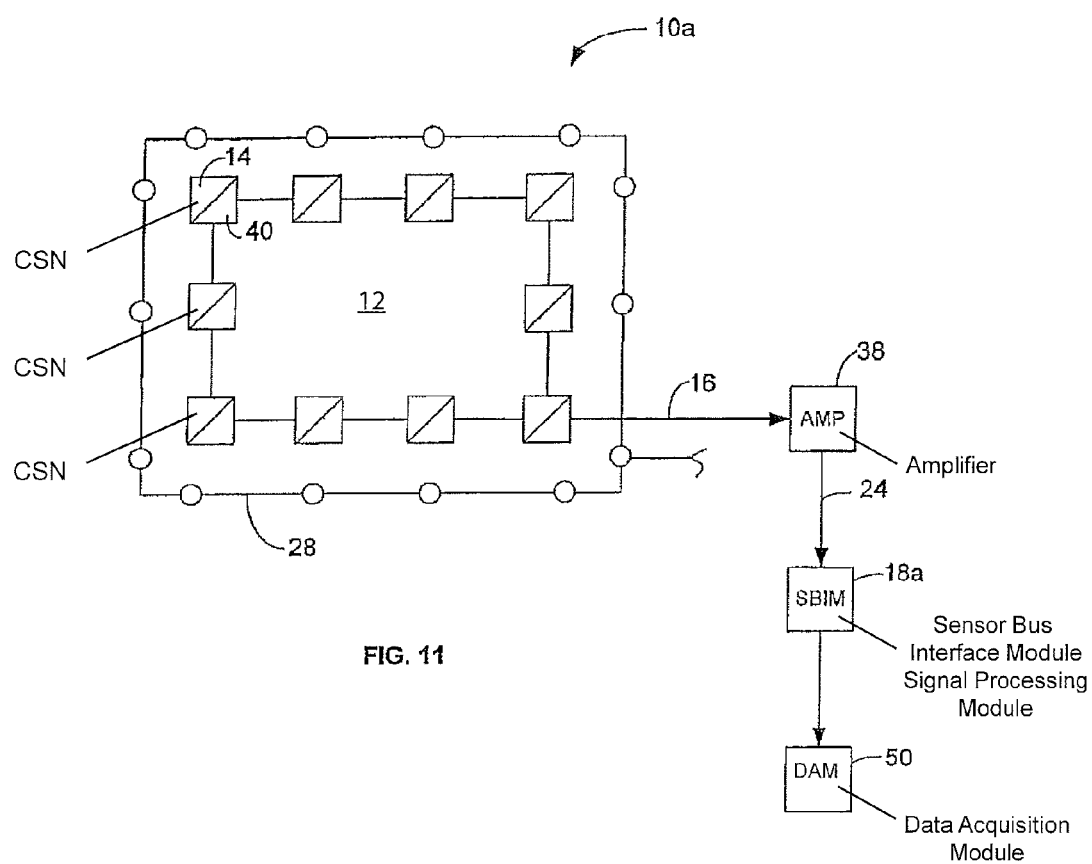
FIG. 11 is a block diagram of a sensor array including a plurality of discrete sensor nodes combined into a single output constructed according to the earlier inventions disclosed in commonly owned U.S. Pat. No. 7,075,424.

As best seen in FIG. 11, a sensor array, generally designated 10a, is shown constructed according to the earlier inventions disclosed in commonly owned U.S. Pat. No. 7,075,424. The sensor array 10a includes three major sub-assemblies: a unit cell 12 having a plurality of discrete sensor nodes 14; a signal adder 16 for combining the output of each of the discrete sensor nodes 14 into a single output; and at least one signal processing module 18a.

The plurality of discrete sensor nodes 14 may further be divided into discrete subgroups, each of the discrete subgroups located at a different structural location. The plurality of discrete sensor nodes 14 are electrically connected in series thereby forming a continuous series connection between each of the discrete sensor nodes.

A number of sensor node configurations are possible, for example, each of the discrete sensor nodes may include a chemical sensor or an accelerometer or a piezoceramic sensor. In one embodiment, the piezoceramic sensor further comprises a plurality of piezoceramic fibers arranged in a planer array wherein the piezoceramic fibers are aligned substantially parallel to each other.

In one embodiment, the signal adder 16 and the signal processing module 18a are connected in series. In addition, the apparatus may further including a signal amplifier 38, such as an impedance matched amplifier, connected between the signal adder 16 and the signal processing module 18a. Further, the apparatus may include a plurality of individual node signal amplifiers 40 connected between each of the discrete sensor nodes 14 and the signal processing module 18a. In one embodiment, each of the node signal amplifiers 40 also is an impedance matched amplifier. Also, in one embodiment, the sensor array may further include a guard array such as a guard ring 28 for improving signal quality.

Figure 12:
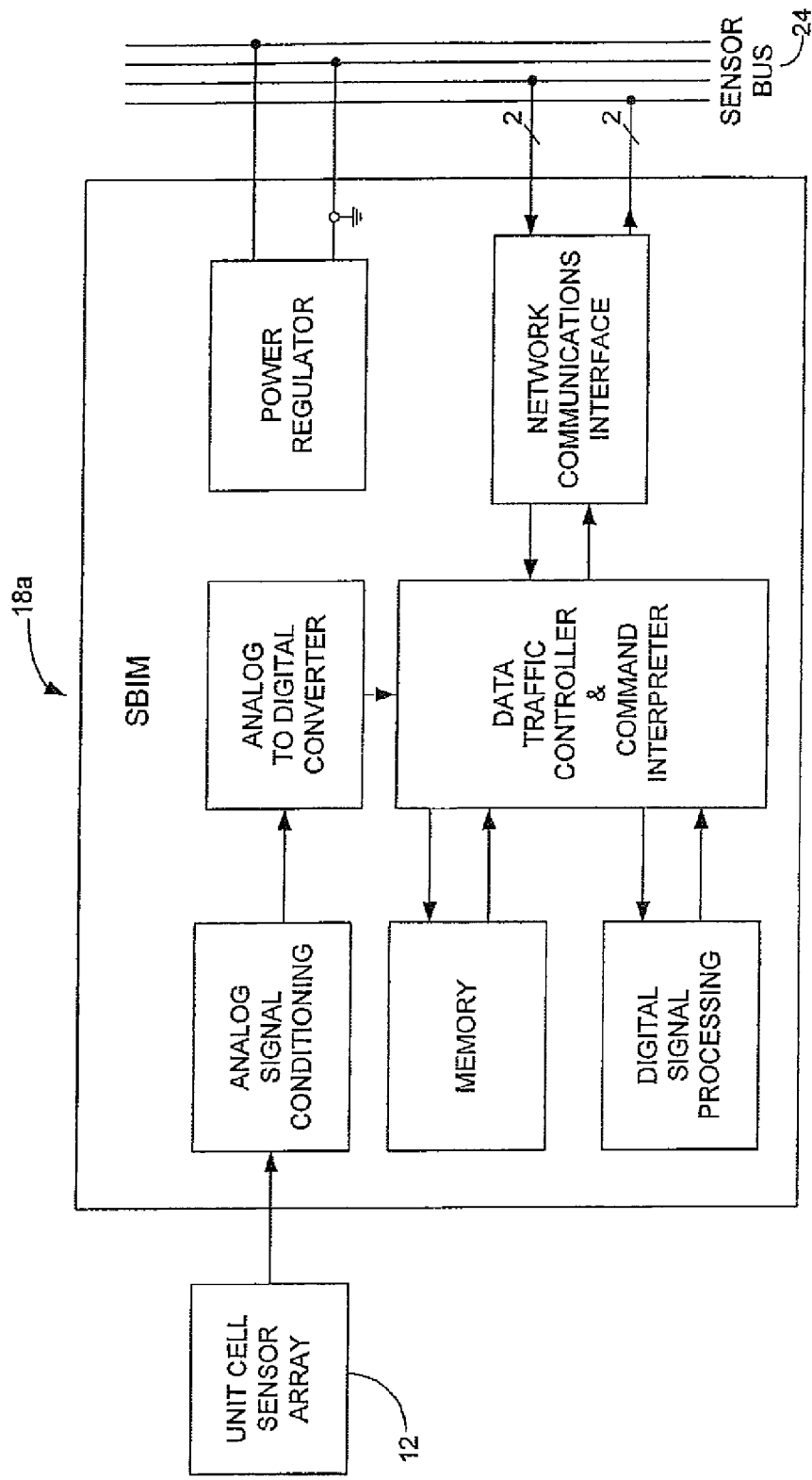
FIG. 12 is a enlarged block diagram of the signal processing module for the sensor array shown in FIG. 11 which is modified from the signal processing module shown in FIG. 3.

Unlike the earlier inventions disclosed in commonly owned U.S. Pat. No. 6,399,939, the earlier inventions disclosed in commonly owned U.S. Pat. No. 7,075,424's signal processing module 18a uses the time interval between the electrical signals from each of the discrete sensor nodes 14 formed into a single sensor array output signal 24 to calculate the location of the critical structural event. As best seen in FIG. 12, the signal processing module 18a includes an input, a filter and an output on a timed scale to calculate the location of the critical structural event. The filter is at a predetermined band width. The predetermined bandwidth is calculated according to the Lamb wave propagation characteristics resulting from the acoustic emission pulse at the source location and by identifying one or more non-dispersive modes of this lamb wave to locate this acoustic emission source. Alternatively, it may be calculated using an electronic tag attached to each sensor that provides the ID number of the first hit sensor.

This process may be understood in greater detail by reference to the following article: Sundaresan, M. J., Schulz, M. J., Ghoshal, A., "Linear Location of Acoustic Emission Sources with a Single Channel Distributed Sensor," Journal of Intelligent Material Systems and Structures, Vol. 12, No. 10, pp. 689-700, October 2001. This paper and all of its references are hereby incorporated by reference in its entirety.

The signal processing module 18*a* conditions the AE signal and performs the data processing. The signal processing module 18*a* itself is made of an analog ASIC (Application Specific Integrated Circuit), for analog signal conditioning, and a digital ASIC which performs the quantification, pattern recognition, timing, and short time data storage.

A special feature of the earlier inventions disclosed in commonly owned U.S. Pat. No. 6,399,939 is that the acoustic emission data processing takes place within the respective signal processing modules 18, and only the processed information is communicated outward through the interface bus 24. Furthermore, the fibers are connected in either series, parallel, or a combined series/parallel configuration to tailor the sensitivity of the sensor nodes 14 and match the environmental conditions under which it is operating.

In the earlier inventions disclosed in commonly owned U.S. Pat. No. 6,399,939 locating damage on a bar needs a minimum of two independent signal processing instrumentation channels and locating damage on a plate needs a minimum of three such instrumentation channels. Thus, when multiple regions of complicated structures such as bridges, aircrafts, and space structures are to be monitored, the number of channels of instrumentation required for the conventional approach becomes numerous and hence unaffordable.

However, in the earlier inventions disclosed in commonly owned U.S. Pat. No. 7,075,424, only one channel of AE instrumentation is required for locating the AE source within a region since the output on a timed scale is used to calculate the location of the critical structural event. Accordingly, instrumentation complexity, cost, and weight can be reduced by at least an order of magnitude, compared to conventional techniques.

Figure 13:
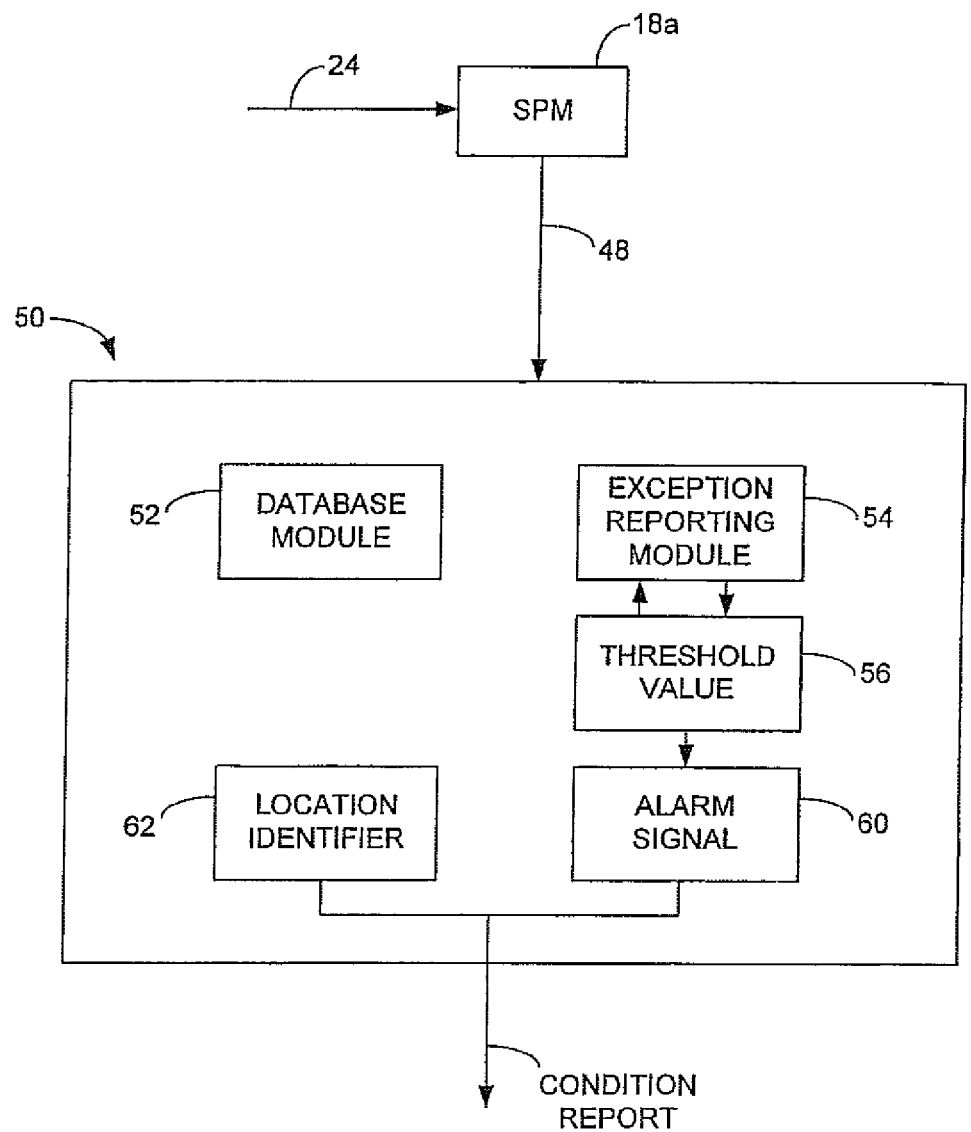
FIG. 13 is a block diagram of a data collection system downstream from the signal processing module also constructed according to the earlier inventions disclosed in commonly owned U.S. Pat. No. 7,075,424.

As best seen in FIG. 13, in the earlier inventions disclosed in commonly owned U.S. Pat. No. 7,075,424, a digital data bus 48 provides communication between the signal processing module 18*a* and the data collection system 50 downstream from the signal processing module 18*a*. The data collection system 50 may include a plurality of various modules for recording and reporting events such as a database module 52 and an exception reporting module 54.

In the earlier inventions disclosed in commonly owned U.S. Pat. No. 7,075,424, the exception reporting module 54 includes a sub-module for setting a predetermined threshold value and a sub-module for sending an alarm when the predetermined threshold value is met. Exception reporting module 54 may further include a station identifier for identifying the location of the alarm.

In operation, three or more piezoceramic (PZT) sensors, PVDF sensors, or other poled capacitive sensors are connected in series and attached to the structure. The output of these sensor nodes 14 are processed so as to extract specific modes of the Lamb waves that are propagating in the structure. After this processing, the signals corresponding to the signal arrival at each of the nodes of the continuous sensor are clearly separated. Further, by using the time interval between the signals from individual nodes, the location of the damage is calculated. The same procedure can be adopted for locating the damage in a plane by using a continuous sensor with a minimum of four sensor nodes. This procedure alone or in combination with neural network algorithm can be used for locating the damage and determining the severity of the damage event.

Thus, in the earlier inventions disclosed in commonly owned U.S. Pat. No. 7,075,424, the number of channels of acoustic emission instrumentation channels required for locating the AE source is reduced from three in the current techniques to one when the time scale algorithms are used for planar AE source location. Also, the number of channels of instrumentations for locating an AE source along a line, such as a pipe, is reduced from two channels to one channel. As a result, a significant reduction in the cost of onboard instrumentation becomes possible.

Detection of acoustic emissions from incremental crack growth plays an important role in structural health monitoring. As a passive system, these sensors can be bonded to a structure and constantly monitor it for emissions that are indicative of crack growth that may be detrimental to the integrity of the structure. Arrays of such sensors can be used to localize the source of the acoustic emissions as well as offer an indication of the speed of crack propagation.

However, acoustic emission technique as described above have been hampered by the presence of spurious signals from sources such as micron scale movement of surfaces fastened together with bolts or rivets. These acoustic emissions from these fretting sources have historically led to false positives that diminish the confidence in the acoustic emission technique.

Simulations performed in the present inventions have shown the presence of the shear mode in acoustic emissions resulting from a triangular impulse representing incremental crack growth. In the simulations, the shear component is shown to be the dominant component at most angles of incidence between the emission source and the sensor. These experiments and simulations have also shown a reduced presence of the shear mode in the acoustic emissions generated by the fretting of two surfaces over one another.

These two findings in combination prompted the applicants to develop sensors sensitive to the shear mode of acoustic emissions as it (a) provides a larger signal over the range of possible angles of incidence and (b) it is a smaller component in fretting signals, which have historically contributed to the prominence of false positives in acoustic emission monitoring schemes.

Figure 14:
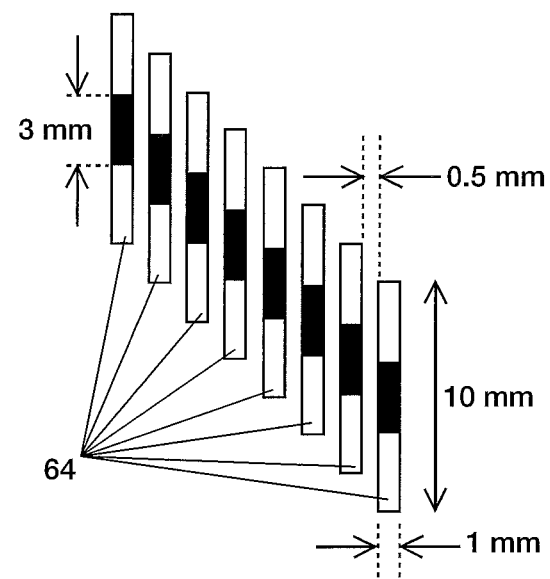
FIG. 14 is a diagram of the piezoelectric strip arrangement of one embodiment of a shear wave sensor optimized for sensing at a 45 degrees position constructed according to the present inventions and a photograph of an actual example of the shear wave sensor.
Figure 14:
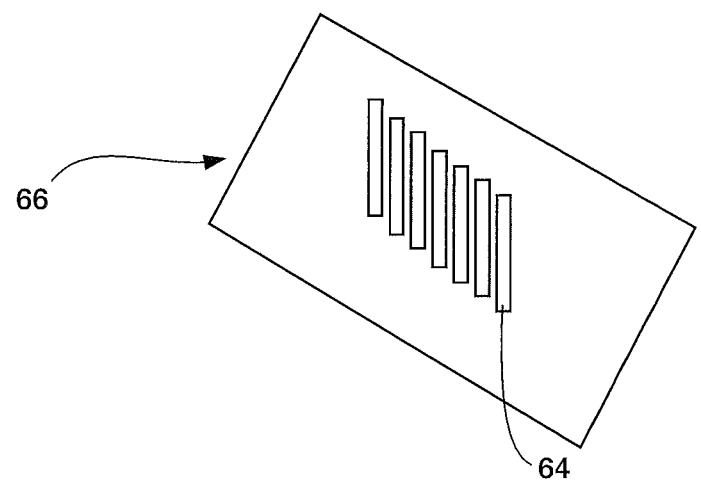

As best seen in FIG. 14, there is shown a diagram of the piezoelectric strip arrangement of one embodiment of a shear wave sensor optimized for sensing at a 45 degrees position constructed according to the present inventions and a photograph of an actual example of the shear wave sensor. The shear wave sensor assemblies 62 were constructed by (a) bonding individual piezoelectric strips 64 to the specimen surface to enable detection of the shear wave, (b) using high aspect ratio strips targeted to acquiring the shear component, and (c) connecting the individual strips 64 together to form a shear wave sensor 66 strip array to generate a single voltage output.

Fabrication of the sensor strip arrays starts with carefully slicing piezoelectric wafers into 10 mm×1 mm strips. The nickel electrode coating on both ends of the top surface was then etched away to leave a 3 mm×1 mm electrical contact in the center. Seven of these individual strips were then arranged parallel to one another with a spacing of 0.5 mm, but with their center points passing through a 45° line as shown in FIG. 14.

The shear wave sensor 66 strip array was then transferred with a piece of tape to the specimen site, which had been roughened with sandpaper before being thoroughly cleaned and dried. A thin layer of Loctite® superglue was spread over the location and the sensor array was held in place until the adhesive set. Care was taken to minimize any adhesive welling up into the gaps between individual strips so that the strips would act as individual strips, independent of stresses experienced by adjacent strips in the array. A copper shim stock was then taped down across the electrical contacts on the strips and Kapton® tape was used to insulate around the shear wave sensor 66 strip array.

Figure 15:
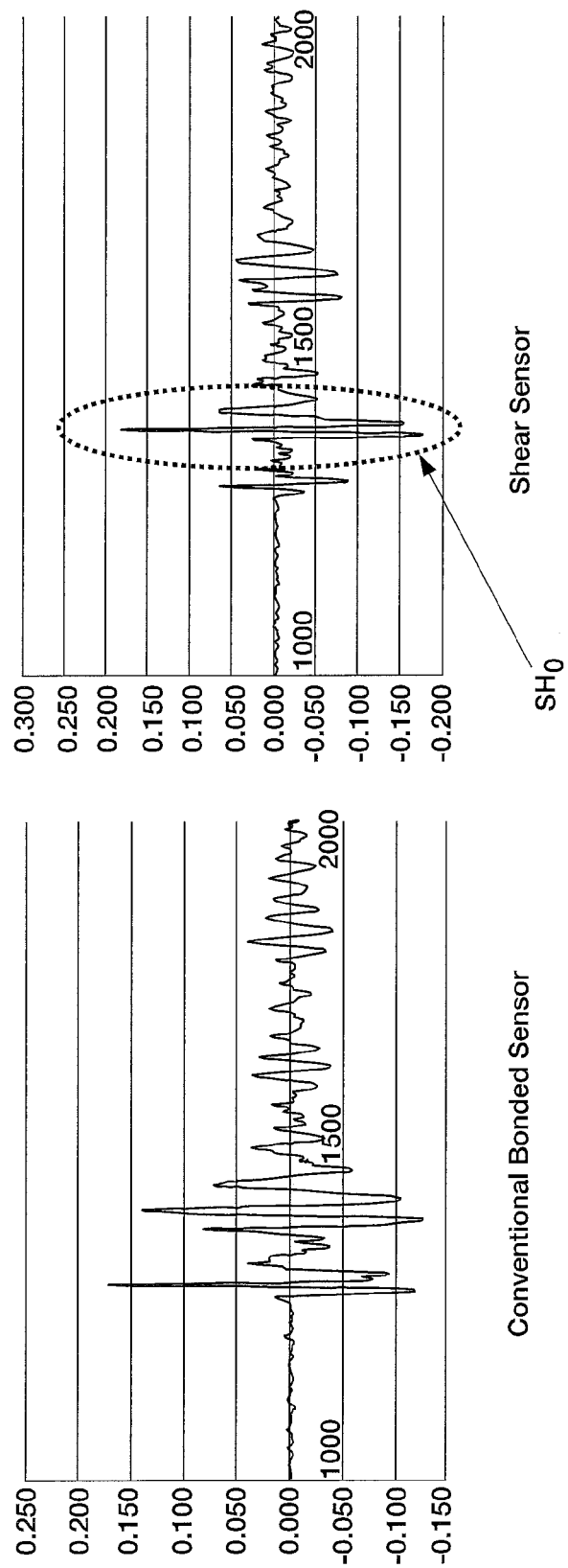
FIG. 15 is a side-by-side comparison of acoustic emissions from fatigue loading as measured by a conventional bonded wafer sensor and a shear wave sensor shown in FIG. 14.

FIG. 15 shows a side-by-side comparison of acoustic emissions from fatigue loading as measured by a conventional bonded wafer sensor and the shear wave sensor shown in FIG. 14. The experiments were carried out on a panel of 2024-T3 aluminum. A conventional PZT sensor was bonded to the specimen perpendicular to the nominal direction of crack growth.

Fatigue loading of the aluminum panel yielded a large number of events that were registered on the shear sensor array, bonded sensor, and resonant sensors. While noise sources did provide many waveforms that could not be confidently attributed to the crack tip region, there were a significant number of events where the triggering of the bonded sensor and shear sensor array was quickly followed by the triggering of the resonant sensors, indicating an origin at or near the crack tip.

In examining many of these groups of waveforms, common patterns were observed where the bonded sensor reported a significant $S_0$ that dominated the waveform while the shear sensor array displayed a shear component that was clearly dominant as shown in FIG. 15.

The above testing procedures may be understood in greater detail by reference to the following article: Sundaresan, M. J., Williams, W. B., "Detection of Shear Waves in an Aluminum Panel," SPIE Smart Structures/NDE Conference, March 2011. This paper and all of its references are hereby incorporated by reference in its entirety.

Figure 16:
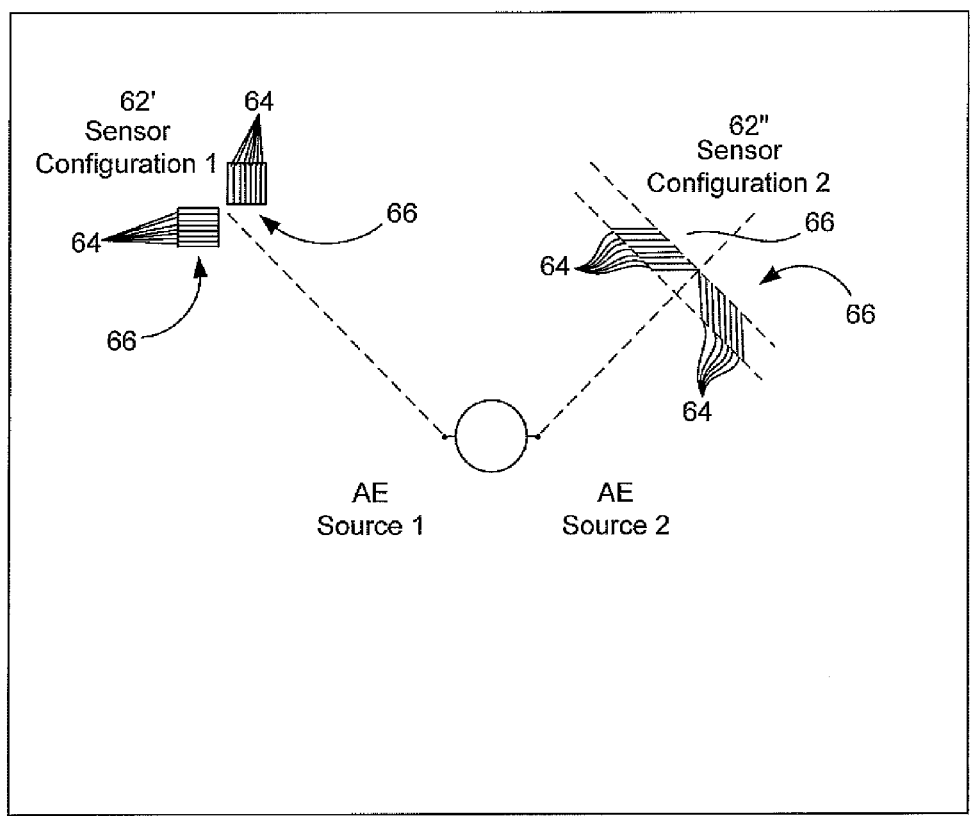
FIG. 16 is a schematic diagram of two different embodiments of shear wave sensors oriented in a plane and at about a 90 degree angle with respect to one another.

Turning now to FIG. 16, there is shown a schematic diagram of two different embodiments of shear wave sensor assemblies oriented in a plane and at about a 90 degree angle with respect to one another. The shear wave sensor assemblies 62 detect hitherto unrecognized component of stress waves generated by crack growth in structural materials as discussed above. When oriented in a plane and at and at about a 90 degree angle with respect to one another, the sensor configuration suppresses other components of the crack growth related stress waves and enhances the shear wave components of the stress waves since $S_o$ and $A_o$ components cancel each other out and substantially only $SH_o$ remains.

By suppressing other components of the stress waves that are common to both crack related acoustic emission signals and extraneous noise signals while, simultaneously enhancing the shear wave components that are unique to crack related acoustic emission signals, the signal to noise ratio for acoustic emission based structural health monitoring techniques as well as other non-destructive examination (NDE) techniques will be substantially increased, thereby reducing false positives.

The presence of shear waves in AE signals or their significance has not been previously recognized. As mentioned above, shear components are generated by incremental crack growth with significant amplitudes. Other sources of AE signals such as fretting related signals and electronic noise do not generate coherent shear waves as the ones produced by the crack growth signals. Hence, identification of the shear component can significantly help in the elimination of false positives in acoustic emission based structural health monitoring applications.

The shear wave sensor 66 that is described in this disclosure is a low profile-type sensor that can be bonded to the surface of structures. This sensor 66 may be made of the same type of material as the bonded wafer sensors that are commonly used in structural health monitoring. Unlike conventional bonded waver sensors, these shear wave sensors 66 are constructed out of strips 64 of PZT material less than 1 mm in width. Such construction is commonly referred to as active fiber composites (AFC) in literature. However, the construction of the present sensors is such that it minimizes or eliminates signals generated by the $S_o$ and $A_o$ modes while maximizing the signal generated by the shear horizontal mode $SH_o$.

The $SH_o$ shear component of the stress wave is usually measured using a traditional ultrasonic shear sensor that is used in nondestructive testing applications. Conventional shear wave sensors are bulky, usually exceeding 12 mm in height and are not suitable for integration into the structures. In addition, previous AFC sensors are used for detecting location of impact of a particle on a plate-like surface, but not for detecting shear waves that are generated by crack growth since the presence of shear waves in AE signals was not recognized.

Turning now to FIG. 17, there is shown is a comparison of the various combinations of bonded wafer AE sensors and shear wave sensors illustrating combinations which reduce false positives and which also may determine location of a structural event. As can be seen, the combination of shear wave sensors adapted to measure the $SH_o$ shear component of the stress wave produced during a structural event may be used in combination with AE sensors for reduced false positive detection and location of such events.

Figure 18:
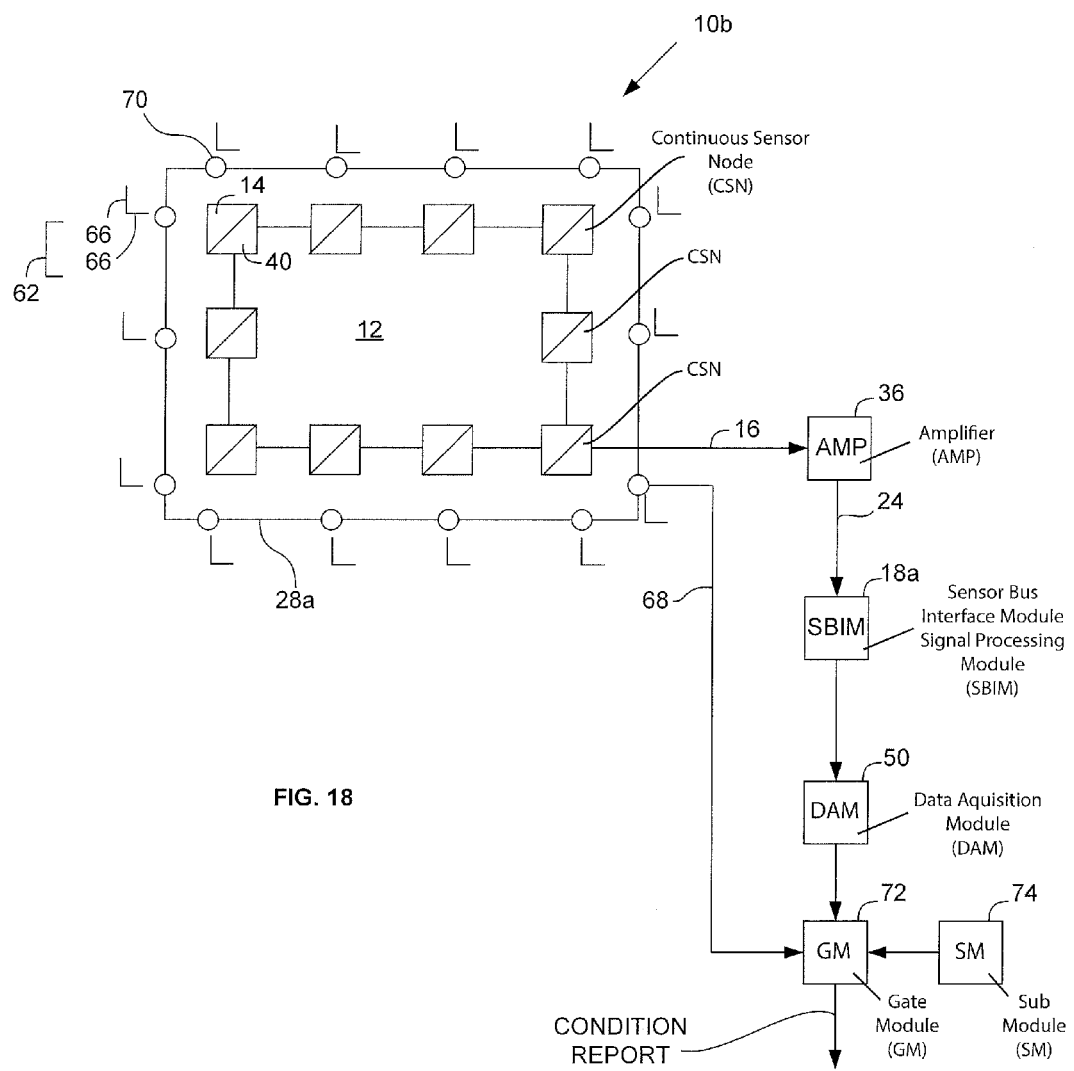
FIG. 18 is a block diagram of a sensor array including a plurality of discrete sensor nodes combined into a single output, which is modified from the signal processing module shown in FIG. 11 to include pairs of shear wave sensors that, in addition, are adapted as a guard ring.

Finally, FIG. 18 is a block diagram of a sensor array 10*b* including a plurality of discrete AE sensor nodes combined into a single output, which is modified from the signal processing module shown in FIG. 11 to include pairs of shear wave sensors 66 that, in addition, may be adapted as a guard ring 28*a*.

As best seen in FIG. 18, a sensor array, generally designated 10*b*, is shown constructed according to the earlier inventions disclosed in commonly owned U.S. Pat. No. 7,075,424. The AE portion of the sensor array 10*b* includes three major sub-assemblies: a unit cell 12 having a plurality of discrete AE sensor nodes 14; a signal adder 16 for combining the output of each of the discrete AE sensor nodes 14 into a single output; and at least one signal processing module 18*a*.

The plurality of discrete AE sensor nodes 14 may further be divided into discrete subgroups, each of the discrete subgroups located at a different structural location. The plurality of discrete AE sensor nodes 14 are electrically connected in series, thereby forming a continuous series connection between each of the discrete AE sensor nodes.

In one embodiment, the signal adder 16 and the signal processing module 18*a* are connected in series. In addition, the apparatus may further including a signal amplifier 38, such as an impedance matched amplifier, connected between the signal adder 16 and the signal processing module 18*a*. Further, the apparatus may include a plurality of individual node signal amplifiers 40 connected between each of the discrete AE sensor nodes 14 and the signal processing module 18*a*. In one embodiment, each of the node signal amplifiers 40 also is an impedance matched amplifier. Also, in one embodiment shown in FIG. 11 above, the sensor array may further include a guard array such as a guard ring 28 for improving signal quality.

As previously discussed regarding FIG. 12 above, the signal processing module 18*a* may include an input, a filter and an output on a timed scale to calculate the location of the critical structural event. The filter is at a predetermined band width. The predetermined bandwidth is calculated according to the Lamb wave propagation characteristics resulting from the acoustic emission pulse at the source location and by identifying one or more non-dispersive modes of this lamb wave to locate this acoustic emission source. Alternatively, it may be calculated using an electronic tag attached to each sensor that provides the ID number of the first hit sensor.

As best seen in FIG. 18, a digital data bus 48 provides communication between the signal processing module 18a and the data collection system 50 downstream from the signal processing module 18a. The data collection system 50 may include a plurality of various modules for recording and reporting events such as a database module 52 and an exception reporting module 54 as well as additional functions as discussed regarding FIG. 11, above.

The sensor array 10b further includes a signal adder electrically connected to a plurality of discrete shear wave sensor nodes 70, the signal adder receiving and combining the electrical signal from each of the discrete shear wave sensor nodes 70 to form a single shear wave output signal 68.

The sensor array 10b may further include a plurality of shear wave sensor assemblies 62, each of the shear wave sensor assemblies including at least one pair of shear wave sensors 66 oriented in a plane and at about a 90 degree angle with respect to one another, wherein the plurality of shear wave sensor assemblies may further be adapted to form a guard array. In one embodiment, the guard array is a guard ring 28a.

A gate module 72 is connected to the AE sensors output from the data collection system 50 and to the shear wave sensor assembly output 68, whereby the gate module is adapted to pass through the electrical signals from the AE sensors to the signal processing module in response to a pre-determined signal from the shear wave sensor assemblies 62. The gate module 72 may further include a sub-module 74 for varying the value of the threshold of the pre-determined signal from the shear wave sensor assemblies 62.

In operation, three or more piezoceramic (PZT) sensors, PVDF sensors, or other poled capacitive sensors are connected in series and attached to the structure. The output of these AE sensor nodes 14 are processed so as to extract specific modes of the Lamb waves that are propagating in the structure. Further, by using the time interval between the signals from individual nodes, the location of the damage is calculated. The gate module 72 connected to the AE sensors output from the date collection system 50 also receives the output from shear wave sensor assemblies 62 and passes through the electrical signals from the AE sensors and the signal processing module in response to a pre-determined signal from the shear wave sensor assemblies.

The present inventions may be used in other areas where stress wave activity is monitored using multiple conventional sensors. This includes, but is not limited to: turbine engines where multiple conventional vibration sensors are used to detect resonant vibrations caused by flow and combustion instabilities; in rotating machinery to detect bearing damage or rotating unbalance; and for detecting damage in structures by monitoring stress wave propagation. In addition, the present inventions may be used for monitoring the structural integrity of airplanes, space vehicles, bridges, and nuclear reactors, as well as other types of pressure vessels, oil rigs, etc.

Certain modifications and improvements will occur to those skilled in the art upon a reading of the foregoing description. It should be understood that all such modifications and improvements have been deleted herein for the sake of conciseness and readability, but are properly within the scope of the following claims.

What is claimed:

1. A sensor array for non-destructively monitoring a structure to detect a critical structural event, said sensor array comprising:
    (a) at least one discrete AE sensor node for producing an electrical signal in response to a structural event;
    (b) at least one shear wave sensor assembly, said shear wave sensor assembly including at least one pair of shear wave sensors, each shear wave sensor of said at least one pair of shear wave sensors having a length to provide a longitudinal axis of the shear wave sensor, and said at least one pair of shear wave sensors being oriented in a plane and at about a 90 degree angle with respect to one another along each sensor's longitudinal axis;
    (c) a gate module connected to said at least one discrete AE sensor node and to said at least one shear wave sensor assembly, whereby said gate module is adapted to pass through said electrical signal from said at least one discrete AE sensor node in response to a pre-determined signal from said at least one shear wave sensor assembly; and
    (d) a signal processing module for receiving and processing said discrete AE sensor output signal.

2. The sensor array according to claim 1, further including a data collection system downstream of said signal processing module.

3. In a sensor array for non-destructively monitoring a structure to detect a critical structural event, said sensor array including at least one discrete AE sensor node for producing an electrical signal in response to a structural event and a signal processing module for receiving and processing said discrete AE sensor output signal, the improvement comprising:
    (a) at least one shear wave sensor assembly, said shear wave sensor assembly including at least one pair of shear wave sensors, each shear wave sensor of said at least one pair of shear wave sensors having a length to provide a longitudinal axis of the shear wave sensor, and said at least one pair of shear wave sensors being oriented in a plane and at about a 90 degree angle with respect to one another along each sensor's longitudinal axis; and
    (b) a gate module connected to said at least one discrete AE sensor node and to said at least one shear wave sensor assembly, whereby said gate module is adapted to pass through said electrical signal from said at least one discrete AE sensor node in response to a pre-determined signal from said at least one shear wave sensor assembly.

4. The sensor array according to claim 3, wherein each of said pair of shear wave sensors oriented in a plane and at about a 90 degree angle with respect to one another include a plurality of discrete shear wave sensor nodes adjacent to one another, each of said discrete shear wave sensor nodes producing an electrical signal in response to a structural event.

5. The sensor array according to claim 4, wherein said plurality of discrete shear wave sensor nodes adjacent to one another are connected in series.

6. The sensor array according to claim 4, wherein said plurality of discrete shear wave sensor nodes are piezoceramic sensors.

7. The sensor array according to claim 6, wherein said piezoceramic sensors are formed into a strip having a length of about 10 mm and a width of about 1 mm.

8. The sensor array according to claim 7, wherein said piezoceramic sensors are active fiber composites.

9. The sensor array according to claim 7, wherein said piezoceramic sensors include a plurality of substantially parallel sensor strips.

10. The sensor array according to claim 9, wherein said plurality of substantially parallel sensor strips are substantially equal length.

11. The sensor array according to claim 10, wherein said plurality of substantially parallel sensor strips of substantially equal length are arranged in a rectangular shape.

12. The sensor array according to claim 10, wherein said plurality of substantially parallel sensor strips of substantially equal length are arranged in a parallelogram shape.

13. The sensor array according to claim 4, further including a signal adder electrically connected to said plurality of discrete shear wave sensor nodes, said signal adder receiving and combining said electrical signal from each of said discrete shear wave sensor nodes to form a single shear wave output signal from each pair of shear wave sensors oriented in a plane and at about a 90 degree angle with respect to one another.

14. The sensor array according to claim 3, further including a plurality of shear wave sensor assemblies, each of said shear wave sensor assemblies including at least one pair of shear wave sensors oriented in a plane and at about a 90 degree angle with respect to one another, wherein said plurality of shear wave sensor assemblies are adapted to form a guard array.

15. The sensor array according to claim 14, wherein said guard array is a guard ring.

16. The sensor array according to claim 3, wherein said gate module connected to said at least one discrete AE sensor node and to said at least one shear wave sensor assembly, whereby said gate module is adapted to pass through said electrical signal from said at least one discrete AE sensor node to said signal processing module in response to a pre-determined signal from said at least one shear wave sensor assembly further includes a sub-module for varying the value of said threshold of said pre-determined signal from said at least one shear wave sensor assembly.

17. A sensor array for non-destructively monitoring a structure to detect a critical structural event, said sensor array comprising:
    (a) at least one discrete AE sensor node for producing an electrical signal in response to a structural event;
    (b) at least one shear wave sensor assembly, said shear wave sensor assembly including a pair of shear wave sensors, each shear wave sensor of said at least one pair of shear wave sensors having a length to provide a longitudinal axis of the shear wave sensor, and said at least one pair of shear wave sensors being oriented in a plane and at about a 90 degree angle with respect to one another along each sensor's longitudinal axis;
    (c) a gate module connected to said at least one discrete AE sensor node and to said at least one shear wave sensor assembly, whereby said gate module is adapted to pass through said electrical signal from said at least one discrete AE sensor node in response to a pre-determined signal from said at least one shear wave sensor assembly;
    (d) a signal processing module for receiving and processing said discrete AE sensor output signal; and
    (e) a data collection system downstream of said signal processing module.

18. The sensor array according to claim 17, wherein the data collection system includes a database module.

19. The sensor array according to claim 18, further including an exception reporting module.

20. The sensor array according to claim 19, wherein said exception reporting module includes a sub-module for setting a predetermined threshold value and a sub-module for sending an alarm when the predetermined threshold value is met.

\* \* \* \* \*